United States Patent [19]

Ballenegger et al.

[11] Patent Number: 4,600,709
[45] Date of Patent: Jul. 15, 1986

[54] BENZODIOXOLE DERIVATIVES, PROCESSES FOR THE MANUFACTURE THEREOF AND CORRESPONDING PHARMACEUTICAL COMPOSITIONS

[75] Inventors: Marc E. Ballenegger, Gimel; Paul Zbinden, Witterswil, both of Switzerland

[73] Assignee: Ciba-Geigy AG, Basle, Switzerland

[21] Appl. No.: 679,661

[22] Filed: Dec. 7, 1984

Related U.S. Application Data

[63] Continuation-in-part of Ser. No. 543,556, Oct. 19, 1983, abandoned.

[30] Foreign Application Priority Data

Oct. 22, 1982 [CH] Switzerland ............ 6163/82
Apr. 6, 1984 [CH] Switzerland ............ 1752/84

[51] Int. Cl.$^4$ .................. A61K 31/36; C07D 317/44
[52] U.S. Cl. .................. 514/228; 514/465; 514/382; 544/158; 548/252; 548/159; 549/436; 549/435; 549/60
[58] Field of Search .................. 549/436; 514/465

[56] References Cited

U.S. PATENT DOCUMENTS 3,872,105  3/1975  Grisar et al. ............ 260/340.5
4,414,214  11/1983  Habicht et al. ............ 549/436
4,501,892  2/1985  Bundy ............ 546/270

Primary Examiner—Ethel G. Love
Attorney, Agent, or Firm—Irving N. Feit

[57] ABSTRACT

The invention relates to novel benzodioxole derivatives of the general formula I

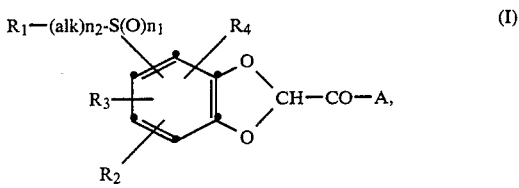

in which
$R_1$ represents an unsubstituted or substituted, aliphatic, aromatic or heteroaromatic radical,
alk represents an alkylene, alkenylene or alkylidene radical having a maximum of 5 carbon atoms,
$n_1$ represents 0, 1 or 2
$n_2$ represents 0 or 1,
$R_2$, $R_3$ and $R_4$ each represents, independently of the others, hydrogen, lower alkyl, lower alkoxy or halogen, and
A represents the radical —O—$R_5$, wherein $R_5$ represents hydrogen or an unsubstituted or substituted, aliphatic or araliphatic hydrocarbon radical, or A represents the radical

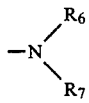

in which either $R_6$ and $R_7$ each represents, independently of the other, hydrogen or lower alkyl, or $R_6$ and $R_7$ are bonded to one another and, together with the adjacent nitrogen atom, represent optionally lower alkyl-substituted tetra- to hexamethyleneimino, 4-morpholinyl or 1H-tetrazol-1-yl, such as, for example, 5-methyl-6-phenylsulphonyl-1,3-benzodioxole-2-carboxylic acid. The invention relates also to salts of compounds of the general formula I in which A represents OR$_5$ wherein R$_5$ represents hydrogen, with bases, and to acid addition salts of compounds of the general formula I in which the radical $R_1$ has a basic character and to processes for the manufacture of the above compounds and the salts thereof and to pharmaceutical compositions containing them. These novel substances have diuretic and supplementary uricosuric action and may be used, preferably in the form of appropriate pharmaceutical compositions, for the treatment of oedema and hypertension.

21 Claims, No Drawings

BENZODIOXOLE DERIVATIVES, PROCESSES FOR THE MANUFACTURE THEREOF AND CORRESPONDING PHARMACEUTICAL COMPOSITIONS

CROSS-REFERENCE

This is a continuation-in-part application of co-pending application Ser. No. 543,556 filed Oct. 19, 1983, now abandoned.

The invention relates to novel benzodioxole derivatives, processes for the manufacture thereof and corresponding pharmaceutical compositions, and to the use of these novel substances and compositions.

The novel compounds according to the invention correspond to the general formula I

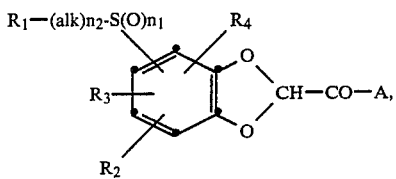

in which
$R_1$ represents an unsubstituted or substituted, aliphatic, aromatic or heteroaromatic radical,
alk represents an alkylene, alkenylene or alkylidene radical having a maximum of 5 carbon atoms,
$n_1$ represents 0, 1 or 2,
$n_2$ represents 0 or 1,
$R_2$, $R_3$ and $R_4$ each represents, independently of the others, hydrogen, lower alkyl, lower alkoxy or halogen, and
A represents the radical —O—$R_5$, wherein $R_5$ represents hydrogen or an unsubstituted or substituted aliphatic or araliphatic hydrocarbon radical, or A represents the radical

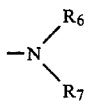

in which either $R_6$ and $R_7$ each represents, independently of the other, hydrogen or lower alkyl, or $R_6$ and $R_7$ are bonded to one another and, together with the adjacent nitrogen atom, represent optionally lower alkyl-substituted tetra- to hexa-methyleneimino, 4-morpholinyl or 1H-tetrazol-1-yl.

The novel compounds may be present in the form of racemates or optical antipodes or, with the appropriate meanings for the variables, alternatively in the form of mixtures of racemates. The invention relates also to salts of compounds of the general formula I in which A represents $OR_5$ wherein $R_5$ represents hydrogen, with bases, and to acid addition salts of compounds of the general formula I in which the radical $R_1$ has a basic character, and also to the manufacture of such salts. Unless otherwise stated, hereinbefore and hereinafter lower radicals or compounds are to be understood as those having a maximum of 7, preferably a maximum of 4, carbon atoms.

An aliphatic radical $R_1$ is especially an alkyl, alkenyl or alkynyl radical having a maximum of 12 carbon atoms, preferably lower alkyl, lower alkenyl or lower alkynyl, such as octyl, nonyl, decyl, undecyl, dodecyl, 2,2,4-trimethyl-1-pentenyl, 1-octynyl or pentyl, isopentyl, hexyl, heptyl, 1-hexenyl, 1-heptenyl or, especially, methyl, ethyl, propyl, isopropyl, butyl, isobutyl, tert.-butylethenyl, 1-methylethenyl, 2-propenyl, 2-butenyl, 2-methyl-2-propenyl, ethynyl or 1-propynyl.

An aromatic radical $R_1$ is especially a 1- or 2-naphthyl radical and above all a phenyl radical. A heteroaromatic radical $R_1$ is preferably a bicyclic radical and especially a monocyclic radical. As a corresponding monocyclic radical, $R_1$ contains especially two nitrogen atoms or, preferably, one nitrogen atom and/or one oxygen or sulphur atom and is, for example, a mono- or di-azacyclic, oxa- or thia-cyclic or oxaza- or thiaza-cyclic radical having 5 ring members, for example 1H-pyrrolyl, such as 1Hpyrrol-2-yl or -3-yl, 1H-pyrazolyl, such as 1H-pyrazol-3-yl, -4-yl or -5-yl, 1H-imidazolyl, such as 1H-imidazol-2-yl, -4-yl or -5-yl, furyl, such as 2- or 3-furyl, thienyl, such as 2- or 3-thienyl, oxazolyl, such as 2-oxazolyl, isoxazolyl, such as 3- or 5-isoxazolyl, thiazolyl, such as 2- or 4-thiazolyl, or a mono- or diazacyclic radical having 6 ring members, for example, pyridyl, such as 2-, 3- or 4-pyridyl, pyridazinyl, such as 3-pyridazinyl, pyrimidinyl, such as 2-, 4- or 5-pyrimidinyl, or 2-pyrazinyl. Corresponding bicyclic radicals $R_1$ comprise, for example, a 5-membered hetero ring of aromatic character having two nitrogen atoms or having one nitrogen atom and/or one oxygen or sulpur atom as ring members and a fused-on benzene ring, or a 6-membered hetero ring of aromatic character having two or, especially, one nitrogen atom(s) as ring member(s) and a fused-on benzene ring. Accordingly, bicyclic heteroaryl is, for example, 1H-indolyl, such as 1H-indol-2-yl, -3-yl, -4-yl, -5-yl or -6-yl, 1H-indazolyl, such as 1H-indazol-3-yl, 1H-benzimidazolyl, such as 1H-benzimidazol-2-yl, -4-yl, -5-yl or -6-yl, benzofuranyl, such as 2-, 3-, 5- or 6-benzofuranyl, benzo[b]thienyl, such as benzo[b]thien-2-yl, -3-yl, -5-yl or -6-yl, benzoxazolyl, such as 2-, 4-, 5- or 6-benzoxazolyl, benzothiazolyl, such as 2-, 4-, 5- or 6-benzothiazolyl, or quinolinyl, such as 2-, 4-, 5- or 6-quinolinyl, isoquinolinyl, such as 1-, 3- or 4-isoquinolinyl, quinazolinyl, such as 2-, 4- or 6-quinazolinyl, quinoxalinyl, such as 2- or 6-quinoxalinyl, or phthalazinyl, such as 1- or 6-phthalazinyl.

As a substituted aliphatic radical, $R_1$ is substituted, for example, by halogen, such as bromine or, especially, fluorine or chlorine, there being mentioned especially polysubstitution at the same carbon atom, that is to say geminal polysubstitution, and substitution at a multiple bond, such as, for example, in trichloromethyl, 2,2,2-trichloroethyl or 2-chloroethenyl. It is also possible for an aliphatic radical $R_1$ to be substituted, for example, by lower alkoxy or lower alkylthio, such as, for example, by the corresponding radicals mentioned below, and then $R_1$ may represent, for example, methoxyethyl, ethoxyethyl or methylthioethyl. As a substituted aromatic or heteroaromatic radical, $R_1$ is substituted one or more times, preferably a maximum of three times, for example by halogen, such as bromine, iodine or, especially, fluorine or chlorine; by lower alkyl, such as, for example, ethyl, propyl, isopropyl, butyl, isobutyl, tert.-butyl or, especially, methyl; by lower cycloalkyl, such as cyclopentyl or, especially, cyclohexyl; by lower alkoxy, lower alkylthio or lower alkylsulphonyl, such as ethoxy, propoxy, isopropoxy, butoxy or isobutoxy, or ethylthio, isopropylthio or butylthio, or ethylsulphonyl, especially methoxy, methylthio and methylsulphonyl;

and/or by trifluoromethyl, hydroxy, lower alkanoyl, lower alkanoylamino, lower alkoxycarbonylamino or lower alkylsulphonylamino, such as, for example, formyl, acetyl, propionyl, butyryl or isobutyryl, or formamido, acetamido, propionamido, butyramido or isobutyramido, or methoxycarbonylamino or ethoxycarbonylamino, or methanesulphonamido or ethanesulphonamido; or by lower alkoxycarbonyl, carbamoyl, mono- or di-lower alkylcarbamoyl, sulphamoyl or mono- or di-lower alkylsulphamoyl, such as, for example, methoxy- or ethoxy-carbonyl, methyl-, ethyl- or isopropylcarbamoyl, dimethyl- or diethyl-carbamoyl, methyl- or ethyl-sulphamoyl or dimethylsulphamoyl.

An alkylene, alkenylene or alkylidene radical alk may be straight-chain or branched and is, for example, 1,1- or 2,2- or 1,2-dimethylethylene, 1-ethylethylene, tetramethylene or 1-propylethylene, or 3,3-dimethylpropenylene, or 1-methylpropylidene, 2-methylpropylidene, butylidene or 1-ethylpropylidene, but especially a radical containing a maximum of 3 carbon atoms, such as ethylene, propylene, trimethylene, or ethenylene, propenylene or 1-methylethenylene, or ethylidene, propylidene, or 1-methylethylidene, and, especially, methylene.

$R_2$, $R_3$ and $R_4$ are, as lower alkyl, for example ethyl, propyl, isopropyl, butyl, isobutyl or tert.-butyl and, especially, methyl; as lower alkoxy, for example ethoxy, propoxy, isopropoxy, butoxy, isobutoxy and, especially, methoxy and, as halogen, bromine, iodine, especially flourine or, more especially, chlorine.

In a radical A, $R_5$ as an unsubstituted or substituted, aliphatic or araliphatic hydrocarbon radical is, for example, alkyl having a maximum of 12 carbon atoms, especially lower alkyl, also 2- or 3-lower alkenyl, or 2-lower alkynyl, lower alkoxy-lower alkyl, halogenated lower alkyl, such as geminal polyhalo-lower alkyl, or, for example, phenyl-lower alkyl or cinnamyl in which the phenyl radical may be substituted, for example in the same manner as a phenyl radical $R_1$. Alkyl $R_5$ is, for example, propyl, isopropyl, butyl, isobutyl, pentyl, isopentyl, neopentyl, hexyl, heptyl, octyl, nonyl, decyl, dodecyl and, especially, methyl or ethyl; lower alkenyl $R_5$ is, for example, allyl, 1- or 2-methallyl, 2-butenyl or 3-butenyl; lower alkynyl is, for example, 2-propynyl; lower alkoxy-lower alkyl is especially 2- or 3-lower alkoxy-lower alkyl, such as, for example, 2-methoxy-, 2-ethoxy-, 2-isopropoxy- or 2-butoxy-ethyl, 2- or 3-methoxypropyl, 2- or 3-ethoxypropyl, also 3- or 4-methoxybutyl or 3- or 4-ethoxybutyl, and halogenated lower alkyl is especially geminally polyhalogenated lower alkyl, that is to say lower alkyl polyhalogenated at the same carbon atom, such as 2,2,2-trifluoro- or 2,2,2-trichloro-ethyl. Phenyl-lower alkyl $R_5$ is, for example, benzyl, 2-phenylethyl, 2- or 3-phenylpropyl or 2-, 3- or 4-phenylbutyl.

As lower alkyl, $R_6$ and $R_7$ may be, for example, the radicals already mentioned as corresponding representatives of $R_5$ and, as optionally lower alkyl-substituted tetra- to hexa-methyleneimino, $R_6$ and $R_7$ together represent, for example, 2- or 3-methyl-1-pyrrolidinyl, 2,5-, 3,3- or 3,4-dimethyl-1-pyrrolidinyl, 1-piperidinyl, 2-, 3- or 4-methyl-1-piperidinyl, 2,6- or 4,4-dimethyl-1-piperidinyl or hexahydro-1H-azepin-1-yl.

Salts of the novel compounds are especially salts of compounds of the general formula I in which A represents hydroxy, that is to say $R_5$ represents hydrogen, with bases, especially pharmaceutically acceptable salts of such compounds with bases. As such salts with bases there come into consideration, for example, alkali metal or alkaline earth metal salts, such as sodium, potassium, calcium or magnesium salts, and also ammonium salts with ammonia or organic amines, such as mono- or di-lower alkylamines, for example methylamine, ethylamine, dimethylamine or diethylamine, or with optionally lower alkylated mono- or di-(hydroxyalkyl)-amines or with tri-(hydroxyalkyl)-amines, for example 2-aminoethanol, 2-(diethylamino)ethanol, 2,2'-iminodiethanol, N-methyl-2,2'-iminodiethanol or 2,2',2''-nitrilotriethanol.

As acid addition salts, especially pharmaceutically acceptable acid addition salts, of compounds of the general formula I in which $R_1$ is of basic character there come into consideration, for example, those with suitable inorganic acids, such as hydrohalic acids, for example hydrochloric acid or hydrobromic acid, and also nitric acid, sulphuric acid or phosphoric acid, or with suitable organic acids, such as carboxylic acids, for example acetic acid, propionic acid, glycolic acid, succinic acid, maleic acid, hydroxymaleic acid, methylmaleic acid, fumaric acid, malic acid, tartaric acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, or organic sulphonic acids, such as lower alkanesulphonic acids optionally containing hydroxy, for example methanesulphonic acid, ethanesulphonic acid, 2-hydroxyethanesulphonic acid or ethane-1,2-disulphonic acid, or arylsulphonic acids, for example benzenesulphonic acid, 4-methylbenzenesulphonic acid or naphthalene-2-sulphonic acid, or other acidic substances, such as ascorbic acid.

The novel compounds of the general formula I and their salts exhibit valuable pharmacological properties. They have, in particular, a diuretic and sodium-diuretic action, in rats in a dosage range of from 1 to 300 mg/kg per os and in dogs in doses of from 1 to 20 mg/kg and above per os, which may be ascertained by collecting the urine over a period of 3 hours after administration (rats) and hourly over a period of 5 hours after administration (dogs) and determining the volume of urine and of sodium, potassium and chlorine ions. In this case the excretion of potassium is increased to a lesser extent than is the excretion of sodium; the good tolerability should also be emphasised.

For example, the administration to rats of 10 mg/kg per os of 5-methyl-6-phenylsulphonyl-1,3-benzodioxole-2-carboxylic acid (6 animals per dose), in comparison with untreated control animals, increases the excretion of sodium ions by a factor of 3.6, of potassium ions by a factor of 1.1 and of chlorine ions by a factor of 2.6. In dogs, for example the administration of 20 mg/kg per os of 5-methyl-6-phenylsulphonyl-1,3-benzodioxole-2-carboxylic acid (4 animals per dose) increases the average excretion per minute measured during the first 5 hours after administration of the active ingredient in comparison with the average excretion per minute during the hour before administration, with regard to sodium ions by a factor of 13.3, with regard to potassium ions by a factor of only 1.5, with regard to chlorine ions by a factor of 10.4 and with regard to the volume of urine by a factor of 3.2. In rats and dogs, the increase in the excretion of potassium ions brought about by the carboxylic acid mentioned is thus very slight compared with the increase in the excretion of sodium ions and chlorine ions.

Furthermore, the compounds of the general formula I exhibit uricosuric activity, as can be seen, for example from experiments on Cebus apes (*Cebus appella*). In these experiments the test animals, under pentobarbital narcosis, are given, by intravenous infusion, polyfructosane in Ringer solution and the test substance in the form of an aqueous solution is injected intravenously in doses of increaseing size. Urine is collected for three 10 minute periods before the first administration of test substance and then after each dose of test substance, and arterial blood is removed before the first collection period and after the last collection period. The uric acid and polyfructosane clearance is calculated from their plasma and urine concentration and finally the fractional excretion of uric acid $FE_{UR}$ is determined as a quotient of the uric acid clearance and glomerular filtration rate. In this test, compounds of the general formula I, such as, for example, 5-methyl-6-phenylsulphonyl-1,3-benzodioxole-2-carboxylic acid, exhibit activity in a dosage range of from 1 to 10 mg/kg i.v. Accordingly, the compounds of the general formula I and their pharmaceutically acceptable salts can be used as potassium-protecting diuretics having supplementary uricosuric action, for example for the treatment of oedema and hypertension.

The invention relates preferably to compounds of the general formula I in which $R_1$ represents an aliphatic hydrocarbon radical that is unsubstituted or substituted by halogen having an atomic number of up to 35, lower alkoxy or lower alkythio and has, in total, that is to say including the substituents, a maximum of 12 carbon atoms, or represents a mono- or bi-cyclic aryl radical that is unsubstituted or substituted by lower alkyl, lower cycloalkyl, lower alkoxy, lower alkylthio, lower alkylsulphonyl, trifluoromethyl, hydroxy, lower alkanoyl, lower alkanoylamino, lower alkoxycarbonylamino and-/or by lower alkylsulphonylamino, or a corresponding heteroaryl radical having a maximum of two nitrogen atoms, or one oxygen or sulfur atom and optionally one nitrogen atom, as hetero ring members, alk, $n_1$, $n_2$, $R_2$, $R_3$ and $R_4$ have the meanings given under formula I and $R_5$ represents hydrogen or an aliphatic or araliphatic hydrocarbon radical having, in total, a maximum of 12 carbon atoms, that is unsubstituted or substituted, in a position higher than the 1- or α-position, by halogen having an atomic number of up to 35, hydroxy or by lower alkoxy, or $R_5$ represents a radical

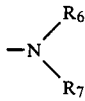

in which $R_6$ and $R_7$ have the meanings given under formula I, and salts of those compounds in which $R_5$ represents hydrogen with bases.

The invention relates especially to compounds of the general formula I in which $R_1$ represents phenyl, thienyl, furyl or ar-benzothiazolyl, each of which is unsubstituted or substituted a maximum of three times by lower alkyl, lower alkoxy, halogen having an atomic number of up to 35, lower alkanoyl and/or by lower alkanoylamino, alk represents alkylene, alkylidene or alkenylene having a maximum of 3 carbon atoms, $R_2$ represents lower alkyl or halogen having an atomic number of up to 35, $R_3$ represents hydrogen, lower alkyl or halogen having an atomic number of up to 35, $R_4$ represents hydrogen and $n_1$, $n_2$ and A have the meanings given under formula I, but $n_1$ represents especially 2, $n_2$ represents especially O and A represents especially $OR_5$ wherein $R_5$ represents hydrogen or lower alkyl, and salts of those compounds in which $R_5$ represents hydrogen with bases.

The invention elates more especially to compounds of the general formula I in which $R_1$ represents phenyl or thienyl, each of which is unsubstituted or substituted a maximum of three times by lower alkyl, lower alkoxy, halogen having an atomic number of up to 35, lower alkanoyl and/or by lower alkanoylamino, alk represents methylene, $n_1$ represents 2, $n_2$ represents 0 and 1, $R_2$ represents lower alkyl, especially methyl, or halogen, especially fluorine or chlorine, $R_3$ represents hydrogen or lower alkyl, especially methyl, $R_4$ represents hydrogen and A represents $OR_5$ wherein $R_5$ represents hydrogen or lower alkyl, and the pharmaceutically acceptable salts of those compounds in which $R_5$ represents hydrogen with bases.

The invention relates more especially to compounds of the general formula I in which $R_1$ represents phenyl that is unsubstituted or substituted a maximum of three times by lower alkyl, lower alkoxy and/or by halogen having an atomic number of up to 35, alk represents methylene, $n_1$ represents 2, $n_2$ represents 0 or 1, $R_2$ represents lower alkyl, especially methyl, or halogen, especially fluorine or chlorine, $R_3$ represents hydrogen or lower alkyl, especially methyl, $R_4$ represents hydrogen and A represents $OR_5$ wherein $R_5$ represents hydrogen or lower alkyl, and the phenylsulphonyl radical is bonded in the 5- or 6-position, and the pharmaceutically acceptable salts of those compounds in which $R_5$ represents hydrogen with bases.

The invention relates above all to compounds of the general formula I in which $R_1$ represents phenyl substituted a maximum of three times by lower alkyl, especially methyl, lower alkoxy, especially methoxy, and/or halogen, especially chlorine, but is especially unsubstituted phenyl, alk represents methylene, $n_1$ represents 2, $n_2$ represents 1 or, especially 0, $R_2$ represents lower alkyl, especially methyl, or halogen, especially chlorine, $R_3$ and $R_4$ represent hydrogen, and A represents $OR_5$ wherein $R_5$ represents hydrogen or lower alkyl, and the phenylsulphonyl radical is bonded in the 5- or 6-position, and the pharmaceutically acceptable salts of those compounds in which $R_5$ represents hydrogen with bases, such as the 5-methyl-6-phenylsulphonyl-1,3-benzodioxole-2-carboxylic acid already mentioned above, and the pharmaceutically acceptable salts thereof with bases.

The novel compounds of the general formula I and salts of those compounds in which A represents $OR_5$ wherein $R_5$ is hydrogen, or that have a basic character, are manufactured in a manner known per se, by (a) reacting a compound of the general formula II

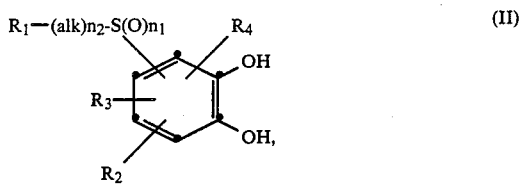

in which $R_1$, alk, $n_1$, $n_2$, $R_2$, $R_3$ and $R_4$ have the meanings given under formula I, or a salt thereof, with a compound of the general formula III

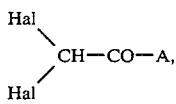

in which Hal represents halogen and A has the meaning given under formula I, or with a salt of such a compound in which A represents OR$_5$ wherein R$_5$ represents hydrogen, or (b) in a compound of the general formula IV

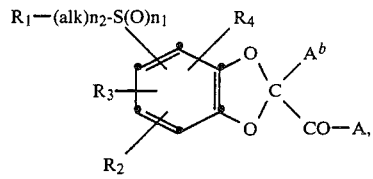

in which A$^b$ represents carboxy, lower alkoxycarbonyl or acetyl, and R$_1$, alk, n$_1$, n$_2$, R$_2$, R$_3$, R$_4$ and A have the meanings given under formula I, replacing the radical A$^b$ by hydrogen, or (c) for the manufacture of a compound of the general formula I in which A has the meaning given under formula I with the exception of a radical OR$_5$ in which R$_5$ represents hydrogen, and R$_1$, alk, n$_2$, R$_3$ and R$_4$ have the meanings given under formula I and n$_1$ represents 1 or 2, reacting a compound of the general formula V

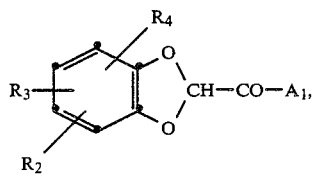

with a compound of the general formula VI

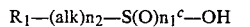

or with an anhydride thereof, in which A$_1$ has the meaning given for A under formula I with the exception of a radical OR$_5$ in which R$_5$ represents hydrogen, n$_1$$^c$ represents 1 or 2 and R$_2$, R$_3$ and R$_4$ and R$_1$, alk and n$_2$ have the meanings given under formula I, or (d) for the manufacture of a compound in which n$_2$ is 1 or R$_1$ is an aliphatic radical according to the definition, and R$_1$ or n$_2$, as the case may be, alk, n$_1$, R$_2$, R$_3$, R$_4$ and A have the meanings given under formula I, reacting a compound of the general formula VIII

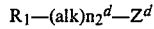

in which Z$^d$ represents a reactively esterified hydroxy group, especially halogen having an atomic number of at least 17, R$_1$ has the meaning given under formula I and, n$_2$ represents 1 or, if R$_2$ is an aliphatic radical, may alternatively be O, or reacting a compound of the general formula VIII

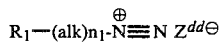

in which Z$^{dd\ominus}$ represents a monovalent anion or the normal equivalent of a polyvalent anion and R$_1$ and n$_1$ have the meanings given under formula I, with a salt of a compound of the general formula IX

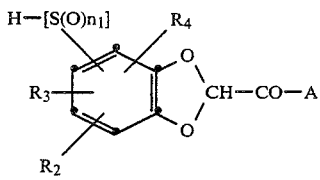

in which n$_1$, R$_2$, R$_3$, R$_4$ and A have the meanings given under formula I, or (e) reacting a metal compound, optionally formed in situ, of the general formula Xa or Xb

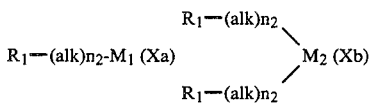

in which M$_1$ represents a monovalent metal ion and M$_2$ represents a divalent metal ion, and R, alk and n$_2$ have the meanings given under formula I, with a compound of the general formula XIa or XIb

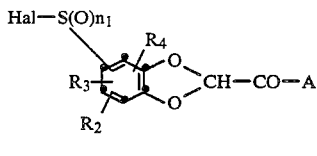

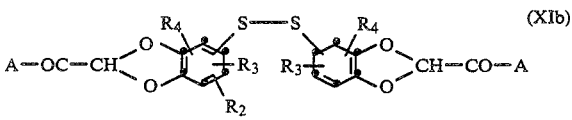

in which Hal represents halogen and n$_1$, R$_2$, R$_3$, R$_4$ and A have the meanings given under formula I, or (f) for the manufacture of a compound of the general formula I in which A represents OR$_5$ wherein R$_5$ represents hydrogen, and R$_1$, alk, n$_1$, n$_2$, R$_2$, R$_3$ and R$_4$ have the meanings give under formula I, or a salt of this compound: in a compound of the general formula XIII

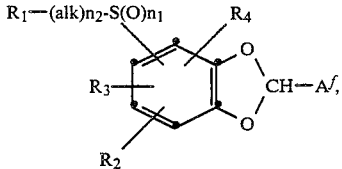

in which A$^f$ represents a group that can be converted into the carboxy group and R$_1$, alk, n$_1$, n$_2$, R$_2$, R$_3$ and R$_4$ have the meanings given under formula I, converting the group A$_f$ into the carboxy group in free or salt form, or (g) for the manufacture of a compound of the general formula I in which A has the meaning given under formula I with the exception of a radical OR$_5$ in which R$_5$ represents hydrogen, and R$_1$, alk, n$_1$, n$_2$, R$_2$ and R$_3$ have the meanings given under formula I: in a compound of the general formula XIV

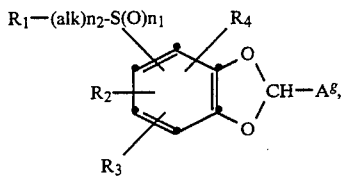

in which $A^g$ represents a radical that can be converted into a radical —CO—$A_1$ in which $A_1$ has the meaning given for A under formula I with the exception of a radical $OR_5$ in which $R_5$ represents hydrogen, and $R_1$, alk, $n_1$, $n_2$, $R_2$, $R_3$ and $R_4$ have the meanings given under formula I, converting the radical $A^g$ into the radical —CO—$A_1$, and (h) if desired, oxidising a compound of the general formula I in which $n_1$ represents 0 or 1 to form the corresponding compound in which $n_1$ represents 1 or 2, or (i) if desired, reducing a compound of the general formula I in which $n_1$ represents 2 or 1 to form the corresponding compound in which $n_1$ represents 1 or 0, and/or, if desired, converting a resulting compound of the general formula I in a different manner known per se into a different compound of the general formula I, and/or separating a compound of the general formula I obtained in the form of a racemate into the optical antipodes, and/or converting a resulting compound of the general formula I in which A represents $OR_5$ wherein $R_5$ represents hydrogen into a salt with a base or freeing such a compound from a resulting salt, or converting a resulting compound of the general formula I having basic character into an acid addition salt or freeing such a compound from a resulting salt.

In the starting materials of the general formula III, Hal is preferably chlorine or bromine, but may also be fluorine or iodine, it also being possible for two different halogen atoms to be present. The reactions according to process (a) are preferably carrried out in organic solvents that are inert under the reaction conditions, for example ethereal solvents, such as, for example, dibutyl ether, 1,2-dimethoxyethane, diethyleneglycol dimethyl ether, tetrahydrofuran or dioxan; alcoholic solvents, such as, for example, methanol, ethanol, isopropanol, butanol, 2-methoxyethanol or 2-ethoxyethanol; or amide-type solvents, such as, for example, dimethylformamide or N,N,N',N',N'',N''-hexamethylphosphoric acid triamide; or in hydrocarbons, such as, for example, petroleum ether, cyclohexane, benzene or toluene. Reactions with free compounds of the general formula II and also with free haloacetic acids of the general formula III are preferably carried out in the presence of basic substances. As such basic substances there may be used, for example, organic or inorganic derivatives of alkali metals or alkaline earth metals: as organic derivatives, there may used, for example, alkali metal or alkaline earth metal alkoxides, such as sodium or lithium methoxide, ethoxide, n-butoxide or tert.-butoxide, or barium methoxide, and as inorganic derivatives, for example, corresponding hydroxides, such as sodium, potassium or calcium hydroxide, or carbonates, such as, for example, sodium or potassium carbonate. In particular carbonates may be used in relatively large excess, for example up to 5-fold excess. When using carbonates, also other organic solvents, such as lower alkanones, for example acetone or 2-butanone, may come into consideration as being sufficiently inert.

Suitable salts of compounds of the general formula II and of the dihaloacetic acids which may be used falling within the scope of the general formula III are, for example, corresponding alkali metal salts or alkaline earth metal salts. The reaction temperatures are, for example, between room temperature and approximately 150° C. and preferably between approximately 70° and 120° C.

Some of the starting materials of the general formulae II and III are known and others may be maufactured analogously to the known compounds. Thus, for example, starting materials of the general formula II may be manufactured by firstly condensing 1,2-dimethoxybenzene, which can be substituted in a manner corresponding to the definition for $R_2$, $R_3$ and $R_4$, with an anhydride of a sulphonic acid of the general formula VI in polyphosphoric acid at elevated temperature, for example at approximately from 100° to 110° C., to form the corresponding sulphone, or with an acyl halide derived from such a sulphonic acid or from a corresponding sulphonic acid, according to the Friedel-Crafts method, for example by means of aluminium chloride in 1,2-dichloroethane at room temperature, to form the corresponding sulphone or corresponding sulphoxide, and cleaving the two methoxy groups in this sulphone or sulphoxide in a manner known per se, for example by heating with pyridine hydrochloride or with 48% hydrobromic acid in acetic acid. If starting materials of the formula II are required in which alk represents a lower alkylidene radical, but especially a 1-lower alkylalkylidene radical, such as the 1-methylethylidene radical, it is possible, after the Friedel-Crafts condensation and before the cleaving of the methoxy groups, to introduce into a sulphone compound in which alk represents methylene or lower alkylidene, one or preferably two lower alkyl radicals, or one lower alkyl radical, respectively, especially methyl, by reaction with a lower alkyl halide, such as methyl iodide, for example in a two-phase system comprising a concentrated aqueous solution of tetrabutylammonium hydroxide or bromide and an inert organic solvent, for example methylene chloride. A process which results directly in dihydroxysulphones of the general formula II and is, therefore, especially advantageous is the reaction of sulphinic acids falling within the scope of the general formula VI, in the form of sodium salts, with 1,2-benzenediols optionally substituted in a manner corresponding to the definition for $R_2$, $R_3$ and $R_4$ in the presence of potassium hexacyanoferrate(III) and sodium acetate in water.

Starting materials of the general formula II in which $n_1$ is O can be manufactured, for example, analogously to process (d).

To carry out process (b), for example a starting material of the general formula IV in which $A^b$ represents carboxy and A, $R_1$, $R_2$, $R_3$ and $R_4$ have the meanings given under formula I is heated in the presence or absence of a catalyst, for example copper powder, and/or of a solvent or diluent, such as, for example, o-dichlorobenzene or 1,2,3,4-tetrahydronaphthalene, until at least an approximately equimolar amount of carbon dioxide has been liberated. Starting materials of the general formula IV in which $A^b$ represents carboxy and A represents $OR_5$ wherein $R_5$ represents hydrogen are manufactured, for example, by hydrolysis of corresponding compounds in which A is $OR_5$ wherein $R_5$ represents lower alkyl, and the substituent in the corresponding position to $A^b$ is lower alkoxy or cyano, in acidic or alkaline medium, for example by heating with a strong mineral acid in an aqueous or aqueous-organic, for example aqueous-lower alkanolic, medium, or with at least twice the molar amount of an alkali metal hydroxide, especially sodium or potassium hydroxide, for example in a lower alkanol, such as methanol, ethanol, isopropanol or n-butanol, or in a lower alkanediol or monoalkyl ether thereof, for example ethyleneglycol, 2-methoxyethanol or 2-ethoxyethanol, water optionally being added to the mentioned solvents in a volume ratio of solvent to water of approximately from 10:1 to 1:2. It is also possible to use water as the reaction medium or, for example, a mixture of water and water-soluble, ethereal solvents, such as dioxan or tetrahydrofuran.

If the hydrolysis is effected in a water-containing mineral acid, the decarboxylation according to the process may be carried out subsequently, that is to say, in the same medium and operation.

Starting materials of the general formula IV in which $A^b$ represents carboxy and A represents a radical corresponding to the definition given under formula I with the exception of a radical $OR_5$ in which $R_5$ represents hydrogen, can be manufactured, for example, by partial hydrolysis in alkaline medium from corresponding compounds having lower alkoxycarbonyl as the radical $A^b$ using an approximately equimolar amount of an alkali metal hydroxide instead of at least twice the molar amount. Another possibility for the manufacture of such starting materials of the general formula IV consists in the hydrogenolysis of corresponding compounds which contain benzyloxycarbonyl in the $A^b$ position.

The dealkoxycarbonylation or deacetylation of corresponding starting materials of the general formula IV, that is to say, those in which $A^b$ represents lower alkoxycarbonyl or acetyl and A represents a radical according to the definition with the exception of a radical $OR_5$ in which $R_5$ represents hydrogen, is effected, for example, by reaction with an approximately equimolar amount of an alkali metal-lower alkoxide in an anhydrous lower alkanol, and if A represents a radical $OR_5$ in which $R_5$ represents lower alkyl, it is preferable to select the same lower alkanol, for example methanol, ethanol or n-butanol, both as component of the starting ester and of the lower alkoxide and as reaction medium. It is also possible, however, to carry out a transesterification by using as reaction medium a relatively high-boiling alkanol that is not the same as the lower alkanol present as the ester component and distilling off a portion thereof simultaneously with the reaction according to the definition, or to allow for only a partial transesterification if the ester of the general formula I formed as a reaction product is not to be used directly as active ingredient but is to be hydrolysed to form the corresponding acid. Instead of a lower alkanol it is also possible to use as a reaction medium, for example, an inert organic solvent, such as, for example, benzene or toluene. The reaction according to the definition is carried out at room temperature or at elevated temperature, for example at the boiling temperature of the reaction medium used. If required, the resulting ester of the general formula I may, as already mentioned in connection with the transesterification, be hydrolysed to form the corresponding acid in the same operation if water is added to the reaction medium.

The starting materials of the general formula IV in which $A^b$ represents lower alkoxycarbonyl or acetyl, and the above-mentioned precursors for compounds of the general formula IV containing carboxy as radical $A^b$ that contain lower alkoxycarbonyl or cyano in the $A^b$ position, can be manufactured analogously to process (a) by reacting compounds of the general formula II in the presence of a base with geminal dihalo compounds that differ from those of the general formula III by the presence of lower alkoxycarbonyl, acetyl or cyano in place of the hydrogen atom located adjacent to two halogen atoms.

According to process (c), for example free sulphonic acids of the general formula VI in polyphosphoric acid or pyrophosphoric acid can be condensed with compounds of the general formula V at elevated temperature, for example at from approximately 80° to approximately 120° C., especially at from approximately 100° to 110° C. It is also possible to condense anhydrides of compounds of the general formula VI, for example the halides thereof, such as chlorides or bromides, also, for example, symmetrical anhydrides thereof, with compounds of the general formula V in the presence of customary Friedel-Crafts condensation agents, such as aluminium chloride or tin(IV) chloride, also, for example, zinc chloride, and also, for example, in concentrated sulphuric acid, phosphoric acid, polyphosphoric acid or pyrophosphoric acid. The above-mentioned acids are preferably used when there is used as starting material a symmetrical anhydride of a sulphonic acid of the general formula VI. When condensation agents are used, the reactions are preferably carried out in a solvent. As such solvents there may be used, for example, halogenated hydrocarbons, such as 1,2-dichloroethane, carbon tetrachloride, methylene chloride or o-dichlorobenzene, and also, for example, aliphatic or cycloaliphatic hydrocarbons, such as heptane or cyclohexane, nitrohydrocarbons, such as nitromethane, nitrocyclohexane or nitrobenzene, and also, under mild conditions, carbon disulphide. The reaction temperature is between approximately $-20°$ C. and $+80°$ C., preferably between approximately 0° and room temperature.

The starting materials of the general formula V may, for their part, be manufactured analogously to process (a) from 1,2-benzenediol, optionally substituted in a manner corresponding to the definition for $R_2$, $R_3$ and $R_4$, such as, for example, 4-methyl-1,2-benzenediol with dihaloacetic acids or functional derivatives thereof corresponding to the general formula III. Some of the sulphonic or sulphinic acids of the general formula IV and functional derivatives of compounds of the general formula VI required as second reactant are known and others may be manufactured analogously to the known acids and derivatives.

Reactions of compounds of the general formula VII, such as, for example, optionally substituted alkyl, alkenyl or alkynyl halides or aralkyl, especially benzyl, halides with salts, especially alkali metal salts, for example sodium or potassium salts, of compounds of the general formula IX are carried out, for example, in water or in an aqueous-organic or organic medium, for example in a lower alkanol, such as methanol or ethanol, preferably at elevated temperature, that is to say, for example, at from approximately 70° to approximately 160°, especially at approximately from 80° to 100°, or at the boiling temperature of the medium or in a closed vessel at a temperature above that temperature. The salt of the compound of the general formula VII can also be formed in situ by adding alkali metal hydroxides or alkali metal salts of weak acids, for example sodium acetate.

The diazonium salts of the general formula VIII are manufactured in customary manner from the corresponding primary amines in which $n_1$ is preferably 0 and $R_1$ is an aromatic radical, for example in aqueous solution by treatment with hydrochloric acid and sodium nitrite, and are reacted while heating and with the addition of sodium hydroxide solution with salts of compounds of the general formula IX optionally formed in situ. Starting materials of the general formulae VII and VIII are known or can be manufactured analogously to the known compounds. Starting materials of the general formula IX are obtained, for example, by reaction of corresponding sulphur-free benzodioxole derivatives of the general formula V with chlorosulphonic acid to form corresponding chlorosulphonyl compounds and by reduction which is known per se to form corresponding sulphinic acids, for example with sodium sulphite, or to form mercaptans, for example with zinc dust and concentrated hydrochloric acid in diethyl ether or an ethereal solvent.

In the process according to (e), there are used as starting materials of the general formula Xa, for example, butyllithium, phenyllithium or 4-methoxyphenyllithium, see, for example, A. Schoönberg et al., Chem. Ber. 66, 237–244 (1933), or alternatively corresponding Grignard compounds, and as starting material of the general formula Xb, for example, diphenylcadmium, bis-(4-chlorophenyl)-cadmium or bis-(4-methoxyphenyl)-cadmium, see, for example, H. R. Henze et al., J. Chem. Soc. 1957, 1410–1413, or diphenyl mercury, and in both cases the process is carried out, for example, in absolute diethyl ether or a different ethereal solvent. Sulphochlorides of the general formula XIa have already been mentioned as precursors for compounds of the general formula IX, as have the corresponding sulphinic acids and mercaptans which can be obtained therefrom by reduction. From the former, sulphinyl chlorides of the general formula XIa are obtained, for example, with thionyl chloride, and from the latter disulphides of the general formula XIb are obtained by oxidation which is known per se.

In the manufacture of compounds of the general formula I in which A represents the radical $OR_5$ wherein $R_5$ represents hydrogen, according to process (f) the conversion of a group $A^f$ into the carboxy group can be effected in a manner known per se, especially by hydrolysis in an alkaline or acidic medium, it being possible in the former case to obtain a salt also directly. Starting materials for the hydrolysis are in the first instance those compounds of the general formula I in which A is not a radical $OR_5$ in which $R_5$ represents hydrogen, especially such compounds which can readily be hydrolysed, such as, for example, the lower alkyl esters, but also other functional derivatives of the carboxylic acids desired as end products, such as, for example, nitriles and imido esters, especially imido-lower alkyl esters, of carboxylic acids falling within the scope of the general formula I. The hydrolysis is effected, for example, in lower alkanolic or aqueous-lower alkanolic alkali hydroxide solutions at from room temperature to approximately 100° C. or the boiling temperature of the reaction medium. Lower alkyl esters, such as methyl or ethyl esters, and other readily cleavable esters of the carboxylic acids falling within the scope of the general formula I can be hydrolysed under even milder conditions, for example in the presence of potassium or sodium carbonate at room temperature or, if necessary, at a slightly elevated temperature, for example 40° C., in an aqueous-organic medium, for example by adding water to the reaction mixture obtained in the reaction according to (a) in a water-miscible solvent, such as, for example, 1,2-dimethoxyethane. From the initially obtained alkali metal salt solutions of the carboxylic acids falling within the scope of the general formula I, it is possible ether to obtain the corresponding pure alkali salt directly by concentration and filtration or concentration by evaporation and recrystallisation, or to free the carboxylic acid first of all and then to purify it, for example by recrystallisation and, if desired, convert it into a salt again with a suitable inorganic or organic base. Functional derivatives of the carboxylic acids falling within the scope of the general formula I may also be converted into the free carboxylic acid of the general formula I in an acidic medium, for example by heating in sulphuric acid diluted with water, for example 60–70% sulphuric acid, or in lower alkanolic-aqueous hydrochloric acid.

The required functional derivatives of carboxylic acids that fall within the scope of the general formula I are manufactured, for example, according to one of the processes mentioned above, and other functional derivatives, such as, for example, nitriles, are manufactured analogously to these processes.

Starting materials of the general formula XIV are, according to the nature of the radical $A^g$ they contain, for example carboxylic acids, carboxylic acid halides or anhydrides, especially mixed anhydrides, and also activated esters, for example cyanomethyl esters, and also lower alkyl esters, that can be reacted, optionally in the presence of condensation agents, with hydroxy compounds of the general formula XV

$$R_5\text{—OH} \qquad (XV)$$

or ammonia or amines of the general formula XVI

$$HN\diagup\!\!\!\diagdown \begin{matrix} R_6 \\ R_7 \end{matrix} \qquad (XVI)$$

in which formulae $R_5$ and $R_6$ and $R_7$ have the meanings given under formula I, or are salts, especially alkali metal or alkaline earth metals salts, of free carboxylic acids, that can be reacted with reactive esters of hydroxy compounds of the general formula XV, such as halides, or organic sulphonic acid esters, for example lower alkanesulphonic or arenesulphonic acid esters, such as methanesulphonic or p-toluenesulphonic acid esters, or alternatively with carbamic acid halides, especially chlorides, derived from amines of the general formula XVI in which the radicals $R_6$ and $R_7$ are other than hydrogen; and also, for example, the imido exters, especially imido-lower alkyl esters, or nitriles, that can be hydrolysed to form esters, especially lower alkyl esters, and to form unsubstituted amides, respectively. Free carboxylic acids can be reacted, for example, also with diazo-lower alkanes to form lower alkyl esters, or with isocyanates that are derived from primary amines falling within the scope of the general formula XVI, to form N-mono-substituted amides.

The reactions of free carboxylic acids with hydroxy compounds of the general formula XV are effected advantageously in the presence of an acidic water-removing catalyst, such as a protonic acid, for example in the presence of hydrochloric or hydrobromic acid, sulphuric acid, phosphoric acid or boric acid, benzenesulphonic or toluenesulphonic acid, or a Lewis acid, for example boron trifluoride etherate, in an excess of the hydroxy compound used and/or in an inert solvent, for example in a hydrocarbon of the benzene series, such as benzene or toluene, a halogenated hydrocarbon, such as chloroform, methylene chloride or chlorobenzene, or in a ethereal solvent, such as tetrahydrofuran, if necessary with removal by distillation, for example azeotropic distillation, of the water freed in the reaction. It is also possible to carry out the reactions in the presence of other water-binding condensation agents, for example in the presence of carbodiimides substituted by hydrocarbon radicals, such as N,N'-diethyl-, N,N'-dicyclohexyl- or N-ethyl-N'-(3-dimethylaminopropyl)-carbodiimide, in inert organic solvents, for example those mentioned above. Halides and mixed anhydrides are reacted, for example, in the presence of acid-binding agents, for example organic, especially tertiary, nitrogen bases, such as, for example, triethylamine, ethyl diisopropylamine or pyridine, or alternatively inorganic bases, for example alkali metal or alkaline earth metal hydroxides or carbonates, such as sodium, potassium or calcium hydroxide or carbonate, in inert organic solvents, for example those mentioned above, and, if necessary, while heating. The reactions of reactive esters of carboxylic acids of the general formula I, for example the cyanomethyl esters, with hydroxy compounds of the general formula XV are carried out, for example, in a solvent that is inert towards the reactants, for example in a hydrocarbon, such as toluene or xylene, an ethereal solvent, such as tetrahydrofuran or dioxan, or alternatively, at moderate temperatures, in an ester, such as ethyl acetate, in a temperature range of from approximately 0° C. to approximately 120° C., preferably at from room temperature to approximately 60° C. For the transesterification of lower alkyl esters of carboxylic acids of the general formula I it is preferable to use hydroxy compounds of the general formula XV having a boiling point clearly above that of the esterified lower alkanol and to carry out the reaction, for example, in an excess of the hydroxy compound and/or in an inert organic solvent that preferably also has a boiling point clearly higher than that of the lower alkanol, preferably in the presence of a catalyst, for example an alkali metal-lower alkoxide, such as sodium or potassium methoxide or ethoxide, at elevated temperature and, preferably, while distilling off the lower alkanol that is liberated. The hydrolysis of imido esters, especially of imido-lower alkyl esters, of carboxylic acids of the general formula I is effected, for example, by means of a water-containing mineral acid, such as hydrochloric or sulphuric acid; and imido ester hydrochlorides obtained, for example, by the addition of hydrogen chloride to nitriles and reaction with anhydrous hydroxy compounds of the general formula XV, especially lower alkanols, can, after the addition of water, be hydrolysed directly to form the corresponding esters, or, for example, the corresponding ester of the general formula I can also be obtained from a mixture of nitrile, hydroxy compound and sulphuric acid having a suitable water content, without isolating the imido ester formed in situ.

The reaction of free carboxylic acids of the general formula I with compounds of the general formula XVI is effected, for example, in the presence of the above-mentioned water-binding agents and in the above-mentioned inert organic solvents, but it is also possible to convert the ammonium salts formed first of all from the free carboxylic acids and the compounds of the general formula XVI into amides of the general formula I by heating, optionally in a suitable organic solvent having a medium or high boiling point, such as, for example, xylene, chlorobenzene or 1,2,3,4-tetrahydronaphthalene, and removal by distillation, optionally azeotropic distillation, of the water liberated in the reaction.

As reactive functional derivatives of carboxylic acids of the general formula I for the reaction with compounds of the general formula XVI and as associated condensation agents and solvents there come into consideration substantially the same derivatives, condensation agents and solvents as those indicated above for reactions with hydroxy compounds of the general formula XV, except that as acid-binding agent and optionally as the only reaction medium, it is possible to use instead of other bases, that is to say tertiary organic bases, alternatively an excess of the compound of the general formula XVI to be reacted. The partial hydrolysis of the corresponding nitriles, mentioned as a further possibility for forming N-unsubstituted amides, may be carried out, for example, by means of water-containing mineral acids, such as hydrochloric acid or dilute sulphuric acid, at room temperature or at moderately elevated temperature.

The free carboxylic acids of the general formula I required as starting materials for process (g) can be manufactured especially according to process (a) or (b), and the reactive functional derivatives thereof can be manufactured, for example, from the free carboxylic acids, in a manner known per se.

The oxidation according to (h) is effected, for example, by means of hydrogen peroxide in an organic or organic-aqueous solvent that is inert with respect to the hydrogen peroxide, such as acetic acid optionally containing water, for example in the mixture resulting from glacial acetic acid and aqueous hydrogen peroxide solution, at moderately elevated temperatures between approximately 60° and 100° C., especially at approximately from 80° to 90° C. and, if a sulphonyl compound corresponding to $n_1=2$ is to be obtained as oxidation product, with more than twice the molar amount of hydrogen peroxide. The oxidation of corresponding thio compounds to form sulphonyl compounds corresponding to $n_1=0$ or 1 is carried out, for example, either according to the above process in a temperature range of approximately from 20° to 60° C. with, if necessary, an amount of hydrogen peroxide that is merely approximately equimolar, or, for example, especially using alkali metal periodate, especially sodium or potassium periodate, such as sodium meta-periodate, in organic-aqueous medium, for example lower-alkanolic aqueous medium, especially ethanolic-aqueous medium, at reduced temperature, for example at from 0° C. to room temperature.

According to process (i), for example compounds of the general formula I in which $n_1$ is 1 can be reduced to form corresponding compounds in which $n_1$ is 0 by means of triphenylphosphine in boiling carbon tetrachloride.

Resulting salt-forming compounds of the formula I can be converted into salts in a manner known per se; for example, those with hydroxy as radical A may be converted with corresponding bases, such as, for example, alkali metal hydroxides, into salts with bases, or those having a basic character may be converter into their acid addition salts. Preferably pharmaceutically acceptable salts are manufactured.

Resulting salts can be converted into the free compounds in a manner known per se, for example by treatment with an acidic reagent, such as a mineral acid, or with a base, for example an alkali metal hydroxide solution, such as sodium hydroxide solution.

The compounds, and their salts, can also be obtained in the form of their hydrates, or their crystals may include the solvent used for crystallisation.

As a result of the close relationship between the novel compounds of the general formula I in which A represents hydroxy in free form and in the form of their salts with bases, and between those compounds in which the radical $R_1$ has basic character in free form and in the form of acid addition salts, hereinbefore and hereinafter the free compounds and their salts shall be understood to mean optionally also the corresponding salts and free compounds, respectively, where appropriate with regard to meaning and purpose.

Depending upon the number of centres of asymmetry and upon the starting materials and procedures chosen, the novel compounds may be obtained in the form of racemates or mixtures of racemates (mixtures of diastereoisomers) or, where desired, also in the form of pure antipodes.

Resulting mixtures of racemates may be separated into the pure racemates or diastereoisomers in known manner, on the basis of the physicochemical differences between the constituents, for example by chromatography and/or fractional crystallisation. Resulting racemates may also be separated into the optical antipodes according to known methods, for example by recrystallisation from an optically active solvent, with the aid of micro-organisms or by reaction of an acidic end product of the general formula I with an optically active base that forms salts with the racemic acid, or by reaction of a basic end product of the general formula I with an optically active acid, and separating the salts obtained in this manner, for example on the basis of differing solubility, into the diastereoisomers, from which the antipodes may be freed by the action of suitable agents. Advantageously the more active of the two antipodes is isolated.

The invention relates to those embodiments of the process according to which a compound obtainable as an intermediate at any stage of the process is used as starting material and the remaining steps are carried out, or a starting material is used in the form of a salt and/or racemate or antipode, or, especially, is formed under the reaction conditions.

The starting materials used in the processes of the present invention are preferably those which result in the compounds described at the beginning as being especially valuable. The present invention relates also to novel starting materials and to processes for their manufacture.

The invention relates also to pharmaceutical preparations that contain compounds of the general formula I as active ingredients, and to processes for their manufacture.

The pharmaceutical preparations according to the invention are for enteral, such as oral or rectal, and for parenteral, administration to warm-blooded animals. The dosage of the active ingredient, which may be administered alone or together with a customary carrier or adjunct, depends upon the species of warm-blooded animal, age and individual condition and upon the method of administration. The daily doses are between 0.15 and 20 mg/kg for mammals, the daily dose for a mammal weighing approximately 70 kg preferably being between 10 and 600 mg, especially between 25 and 300 mg, depending on individual condition and age. Appropriate oral dosage unit forms, for example dragées, tablets or capsules, contain preferably from 5 to 150 mg, especially from 10 to 100 mg, of an active ingredient according to the invention, that is to say, a compound of the general formula I or a pharmaceutically acceptable salt of a compound of the general formula I that is capable of salt formation, together with pharmaceutical carriers.

The pharmaceutical preparations of the present invention are manufactured in a manner known per se, for example by means of conventional mixing, granulating, confectioning, dissolving of lyophilising processes. For example, pharmaceutical preparations for oral use can be obtained by combining the active ingredient with solid carriers, optionally granulating a resulting mixture and processing the mixture or granulate, if desired or necessary after the addition of suitable adjuncts, to form tablets or dragée cores.

Suitable carriers are especially fillers, such as sugar, for example lactose, saccharose, mannitol or sorbitol, cellulose preparations and/or calcium phosphates, for example tricalcium phosphate or calcium biphosphate, also binders, such as starch pastes using, for example, maize, wheat, rice or potato starch, gelatine, tragacanth, methylcellulose and/or polyvinylpyrrolidone, and/or, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dragée cores are provided with suitable coatings that are optionally resistant to gastric juices, there being used, inter alia, concentrated sugar solutions which may contain gum arabic, talc, polyvinylpyrrolidone, polyethylene glycol and/or titanium dioxide, lacquer solutions in suitable organic solvents or mixtures of solvents or, for the production of coatings that are resistant to gastric juices, solutions of suitable cellulose preparations, such as acetylcellulose phthalate or hydroxypropylmethylcellulose phthalate. Dyes or pigments can be added to the tablets or dragée coatings, for example for identification purposes or to indicate different doses of active ingredient.

Further pharmaceutical preparations for oral administration are dry-fill capsules consisting of gelatine and also soft sealed capsules consisting of gelatine and a plasticiser, such as glycerine or sorbitol. The dry-fill capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, it being possible also to add stabilisers.

As rectally administrable pharmaceutical preparations there come into consideration, for example, suppositories which consist of a combination of the active ingredient with a suppository base. Suitable suppository bases are, for example, natural or synthetic triglycerides, paraffin hydrocarbons, polyethylene glycols and higher alkanols. It is also possible to use gelatine rectal capsules which contain a combination of the active ingredient with a base material; as base materials there come into consideration, for example, liquid triglycerides, polyethylene glycols and paraffin hydrocarbons.

Especially suitable for parenteral adminstration are aqueous solutions of an active ingredient in water-soluble form, for example a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspension that contain substances which increase the viscosity, for example sodium carboxymethylcellulose, sorbitol and/or dextran, and, optionally, stabilisers.

The invention relates also to the use of the novel compounds of the formula I and the pharmaceutically acceptable salts thereof as pharmacologically active compounds, especially as diuretics having supplementary uricosuric action, preferably in the form of pharmaceutical preparations, in a method for the prophylactic and/or therapeutic treatment of the human or animal body, especially for the treatment of oedema and/or hypertension.

The following Examples illustrate the invention described above but are not intended to limit its scope in any way. Temperatures are given in degrees Centigrade.

EXAMPLE 1

27.7 g (200 mmol) of anhydrous potassium carbonate are added to a suspension of 10.6 g (40 mmol) of 4-methyl-5-phenylsulphonyl-1,2-benzenediol in 65 ml of cold 1,2-dimethoxyethane. While stirring vigorously, a solution of 7.85 g (50 mmol) of dichloroacetic acid ethyl ester in 5 ml of 1,2-dimethoxyethane is added dropwise thereto in the course of 30 minutes. The mixture is stirred for a further hour at room temperature and is then boiled under reflux for 3 hours while stirring. It is then cooled to 30°, water is added, and the whole is stirred for 30 minutes and adjusted to pH 1-2 with hydrochloric acid. Some of the 1,2-dimethoxyethane is removed in a rotary evaporator and the solution remaining is extracted three times with ethyl acetate. The combined ethyl acetate solutions are washed with water, and then with saturated sodium chloride solution, dried over sodium sulphate, treated with activated carbon and concentrated by evaporation. The resulting yellow-green oil is crystallised from ethyl acetate/hexane. The sand-coloured crystals are dissolved in ethyl acetate and treated again with activated carbon. The solvent is removed in a rotary evaporator. The yellow oil remaining is crystallised from methylene chloride at 0°, yielding 5-methyl-6-phenylsulphonyl-1,3-benzodioxole-2-carboxylic acid having a melting point of 169°-171°.

The starting material can be produced as follows:

(a) A solution of 50 g (152 mmol) of potassium hexacyanoferrate (III) and 95 g of sodium acetate trihydrate in 200 ml of water is added dropwise in the course of 30 minutes, at room temperature under nitrogen, to a solution of 16.4 g (100 mmol) of the sodium salt of benzenesulphinic acid and 13.6 g (110 mmol) of 4-methyl-1,2-benzenediol in 150 ml of water. After stirring for 1½ hours, the reaction mixture is acidified and repeatedly extracted with ethyl acetate. The combined organic phases are washed with water and saturated sodium chloride solution, dried over sodium sulphate and concentrated by evaporation. The residue is recrystallised from ether/hexane, yielding 4-methyl-5-phenylsulphonyl-1,2-benzenediol having a melting point of 145°-149°.

EXAMPLE 2

A mixture of 20.8 g (100 mmol) of 5-methyl-1,3-benzodioxole-2-carboxylic acid ethyl ester, 18.2 g (105 mmol) of the sodium salt of benzenesulphonic acid, 200 g of polyphosphoric acid and 85 ml of methanesulphonic acid is stirred vigorously for 4 days at 25° under nitrogen. 500 ml of ice-water are then added to the reaction mixture while cooling with ice, and the whole is extracted four times with ether. The combined organic phases are washed first with water, then with a saturated sodium chloride solution, dried over sodium sulphate and concentrated to dryness by evaporation. The 5-methyl-6-phenylsulphonyl-1,3-benzodioxole-2-carboxylic acid ethyl ester remaining is purified by column chromatography over silica gel using as eluant ethyl acetate/hexane in a ratio of 1:1. The fractions containing uniform substance are combined and concentrated by evaporation. The yellow oily residue crystallises on standing. It is stirred for two hours at 0° with ether, filtered, washed with cold ether and dried. The ester, crystallising into bright yellow needles, melts at 89°-90°.

8.6 g (24.7 mmol) of 5-methyl-6-phenylsulphonyl-1,3-benzodioxole-2-carboxylic acid ethyl ester are suspended in 37 ml of methanol. 37 ml of 1N sodium hydroxide solution are then slowly added at room temperature, the starting material soon dissolving. After one hour the reaction mixture is cooled, concentrated hydrochloric acid is added and the whole is extracted three times with ethyl acetate. The combined organic phases are washed with water and then with a saturated sodium chloride solution, dried over sodium sulphate and concentrated by evaporation. 50 ml of methylene chloride are added to the yellow oil remaining, and the whole is stirred until crystallisation occurs. The filtered crystals are recrystallised from a small amount of 1,2-dichloroethane, yielding 5-methyl-6-phenylsulphonyl-1,3-benzodioxole-2-carboxylic acid in the form of white crystals having a melting point of 169°-171°.

The 5-methyl-1,3-benzodioxole-2-carboxylic acid ethyl ester used as starting material can be produced, for example, in accordance with one of the two processes described below:

(a) A solution of 38.7 g (0.3 mol) of dichloroacetic acid, 12 g (0.3 mol) of sodium hydroxide, 40 ml of water and 0.6 g of Aliquat is stirred under nitrogen and heated to 95°. At this temperature, there is added dropwise thereto, in the course of 2½ hours in a uniform manner, a solution of 24.8 g (0.2 mol) of 4-methyl-1,2-benzenediol (homopyrocatechol), 100 ml of water and 20 g (0.5 mol) of sodium hydroxide, which has been produced beforehand under nitrogen. The whole is further stirred for 1½ hours at 95° and then cooled to room temperature. The reaction mixture is acidified to pH 8 with hydrochloric acid and washed twice with ether. The aqueous phase is then adjusted to pH 1-2 with concentrated hydrochloric acid and extracted with ether. The combined ether solutions are washed with water and saturated sodium chloride solution, dried over sodium sulphate and concentrated completely by evaporation in a rotary evaporator.

The crude 5-methyl-1,3-benzodioxole-2-carboxylic acid obtained as residue in (a) is dissolved in 400 ml of anhydrous ethanol and boiled for 2 hours with 0.5 ml of concentrated hydrochloric acid. The solution is concentrated to a large extent and the resulting crude ester is dissolved in ether or methylene chloride. The solution is washed with saturated sodium bicarbonate solution, water and saturated sodium chloride solution, dried over sodium sulphate and concentrated to dryness by evaporation. The crude product remaining, which is in the form of a brown oil, is distilled under a water jet vacuum, the 5-methyl-1,3-benzodioxole-2-carboxylic acid ethyl ester passing over at 105°–108°/5 mbar.

(b) A solution of 6.2 g (50 mmol) of 4-methyl-1,2-benzenediol in 20 ml of dimethylformamide is added to a suspension of 34.6 g (250 mmol) of anhydrous potassium carbonate in 150 ml of dimethylformamide. After 5 minutes, there is added thereto, in the course of 15 minutes, a solution of 12 g (55 mmol) of dibromoacetic acid in 25 ml of dimethylformamide, and the whole is heated at 80° for 4 hours. Water is then added to the reaction mixture and the whole is acidified and repeatedly extracted with ethyl acetate. The combined extracts are washed with water and with saturated sodium chloride solution, dried over magnesium sulphate and concentrated by evaporation. The residue is esterified in the manner described in (a) with ethanol in the presence of a small amount of concentrated hydrochloric acid.

EXAMPLE 3

In a manner analogous to that described in Example 1, a mixture of 27.1 g (196 mmol) of potassium carbonate, 12.5 g (39.16 mmol) of 4-chloro-5-(2-chlorophenylsulphonyl)-1,2-benzenediol and 6.76 g (43.08 mmol) of dichloroacetic acid ethyl ester in 200 ml of 1,2-dimethoxyethane is boiled under reflux for 15 hours. The solid material, which has settled on the wall, is scratched away, a further 27.1 g (196 mmol) of potassium carbonate and 6.76 g (43.08 mmol) of dichloroacetic acid ethyl ester are added and the whole is boiled under reflux for a further 8 hours. The reaction mixture is poured onto ice/water, acidified and extracted with ethyl acetate. After concentration by evaporation, the 5-chloro-6-(2-chlorophenylsulphonyl)-1,3-benzodioxole-2-carboxylic acid remaining, which is in the form of a brown oil, is brought to crystallisation in acetonitrile and recrystallised once more from acetonitrile, resulting in white crystals having a melting point of 226°–227°.

The required 4-chloro-5-(2-chlorophenylsulphonyl)-1,2-benzenediol is produced as follows:

(a) 24.6 g (170 mmol) of 4-chloro-1,2-benzenediol are added while stirring, under nitrogen, to a solution of 28.8 g (163 mmol) of 2-chlorobenzenesulphinic acid (obtained by the reduction of 2-chlorobenzenesulphonyl chloride with sodium sulphite) in 163 ml of 1N sodium hydroxide solution. In the course of 40 minutes there is added dropwise thereto, at room temperature, a solution of 82 g (240 mmol) of potassium hexacyanoferrate (II) and 150 g of sodium acetate trihydrate in 300 ml of water. The solution becomes turbid and an oil forms which, after stirring for 2 hours, crystallises. The reaction mixture is extracted three times with ethyl acetate. The organic phases are washed with water and saturated sodium chloride solution, dried and concentrated by evaporation. The crude brown crystals are dissolved in warm isopropanol and treated with activated carbon. The solution is filtered, concentrated to 200 ml, added dropwise to 800 ml of ice-cold water and stirred for 2 hours while cooling with ice. The white suspension is filtered with suction, and the filtration residue is washed with water and dried, yielding 4-chloro-5-(2-chlorophenylsulphonyl)-1,2-benzenediol in the form of white crystals having a melting point of 226°–229°.

EXAMPLE 4

A suspension of 12.0 g (43.1 mmol) of 4-methyl-5-(4-methylphenylsulphonyl)-1,2-benzenediol and 30 g (216 mmol) of freshly calcined potassium carbonate in 200 ml of dry 1,2-dimethoxyethane is stirred for 5 minutes, under nitrogen, using a high-speed stirrer. In the course of this the temperature rises to 75°. Then, while stirring moderately (propeller stirrer), there is added dropwise thereto, in the course of one hour, a solution of 6.77 g (43.1 mmol) of dichloroacetic acid ethyl ester in 50 ml of dry 1,2-dimethoxyethane and the mixture is then boiled under reflux for 15 hours. It is subsequently poured onto an ice/water mixture and adjusted to pH 1–2 with concentrated hydrochloric acid. Some of the 1,2-dimethoxyethane is evaporated off in a rotary evaporator and the solution remaining is extracted with ethyl acetate. The combined organic phases are washed with water and saturated sodium chloride solution, dried over sodium sulphate and concentrated by evaporation in a rotary evaporator. The resulting black oil is dissolved in ethanol, 0.5 g of p-toluenesulphonic acid is added, and the whole is boiled under reflux in a vessel provided with a Soxhlet attachment that is filled with molecular sieve. The ethanolic solution is then concentrated completely by evaporation and chromatographed over silica gel (solvent ethyl acetate/hexane in a ratio of 1:1). The uniform fractions containing the desired substance are combined and concentrated by evaporation. In this manner 5-methyl-6-(4-methylphenylsulphonyl)-1,3-benzodioxole-2-carboxylic acid ethyl ester is obtained in the form of a yellow oil, which can be hydrolysed directly.

A solution of 10 g of 4-methyl-5-(4-methylphenylsulphonyl)-1,3-benzodioxole-2-carboxylic acid ethyl ester in 30 ml of methanol is cooled to 5°. 41.3 ml of 1N sodium hydroxide solution are added thereto under nitrogen, while stirring, the temperature rising to 30°. The mixture is cooled to 20° and stirred at room temperature for 30 minutes. Ice-water is then added, the whole is filtered, and the filtrate is adjusted to pH 1–2 with concentrated hydrochloric acid and extracted three times with ethyl acetate. The combined ethyl acetate phases are washed with water and with a saturated sodium chloride solution, dried over sodium sulphate and concentrated completely by evaporation. The residue is crystallised from acetonitrile. The crystallisate is stirred with cold ether, then filtered and dried. The resulting 5-methyl-6-(4-methylphenylsulphonyl)-1,3-benzodioxole-2-carboxylic acid melts at 162°–165°.

The required 4-methyl-5-(4-methylphenylsulphonyl)-1,2-benzenediol is produced as follows:

(a) Under nitrogen, a mixture of 500 g of polyphosphoric acid and 47.6 g (250 mmol) of p-toluenesulphonic acid monohydrate is heated to 100° and then added to 41.9 g (275 mmol) of 1,2-dimethoxy-4-methylbenzene (4-methylveratrole). The reddish suspension is stirred at 105° for 30 minutes, cooled to 80°, 1500 ml of water are added and the whole is cooled to room temperature. The reaction mixture is extracted with ethyl acetate. The organic phase is washed with water, dried, treated with activated carbon and concentrated by evaporation. The resulting solid substance is recrystallised from toluene, but can also be further reacted directly. The 1,2-dimethoxy-4-methyl-5-(4-methylphenylsulphonyl)benzene is obtained from toluene in the form of white crystals having a melting point of 133°–134.5°.

(b) 326 g of anhydrous pyridine hydrochloride are heated to 180°. While stirring, 33 g (113 mmol) of 1,2-dimethoxy-4-methyl-5-(phenylsulphonyl)-benzene are rapidly added. The reaction mixture is heated at 190° for a further 15 minutes and stirred at this temperature for one hour. The hot reaction mixture is poured onto an ice/water mixture and extracted three times with ether. The ether phases are combined, washed with water and saturated sodium chloride solution, dried over sodium sulphate and concentrated by evaporation in a rotary evaporator. In this manner, dark-brown crystals are obtained, which are crystallised from ether/hexane. 1,2-Dimethoxy-4-methyl-5-(phenylsulphonyl)-benzene having a melting point of 162°–163° is thus obtained in the form of sand-coloured crystals. These crystals are used further without additional purification.

EXAMPLE 5

In a manner analogous to that described in Example 4, using 25.0 g (83.7 mmol) of 4-(4-chlorophenylsulphonyl)-5-methyl-1,2-benzenediol, 13.2 g (83.7 mmol) of dichloroacetic acid ethyl ester, 57 g (418 mmol) of potassium carbonate and 220 ml of 1,2-dimethoxyethane, with subsequent hydrolysis with sodium hydroxide solution in methanol, the desired 5-(4-chlorophenylsulphonyl)-6-methyl-1,3-benzodioxole-2-carboxylic acid is obtained in the form of white crystals having a melting point of 169°–171° (from 1,2-dichloroethane).

The required 4-(4-chlorophenylsulphonyl)-5-methyl-1,2-benzenediol is produced as follows:

(a) 27.9 g (224.6 mmol) of 4-methyl-1,2-benzenediol are added while stirring, under nitrogen, to a solution of 35.0 g (198.2 mmol) of 4-chlorobenzenesulphinic acid (obtained by reduction of 4-chlorobenzenesulphonyl chloride with sodium sulphite) in 198.2 ml of aqueous 1N sodium hydroxide solution. There is added dropwise thereto at room temperature, in the course of 40 minutes, a solution of 109 g (330.3 mmol) of potassium hexacyanoferrate (III) and 198.2 g of sodium acetate trihydrate in 400 ml of water. After stirring for 1½ hours, the reaction mixture is acidified and extracted with ethyl acetate. The combined organic phases are washed with water and saturated sodium chloride solution, dried over sodium sulphate and concentrated by evaporation. The solid residue is recrystallised from 1,2-dichloroethane. The 4-(4-chlorophenylsulphonyl)-5-methyl-1,2-benzenediol so obtained melts at 184°–186°.

EXAMPLE 6

In a manner analogous to that described in Example 4, there is obtained by condensation of 25.0 g (72.2 mmol) of 4-(4-cyclohexylphenylsulphonyl)-5-methyl-1,2-benzenediol with 11.3 g (72.7 mmol) of dichloroacetic acid ethyl ester and 50 g (361 mmol) of potassium carbonate in 190 ml of 1,2-dimethoxyethane and subsequent hydrolysis with sodium hydroxide solution in methanol, 5-(4-cyclohexylphenylsulphonyl)-6-methyl-1,3-benzodioxole-2-carboxylic acid in the form of white crystals having a melting point of 159°–161.5° (from ethyl acetate/hexane).

The 4-(4-cyclohexylphenylsulphonyl)-5-methyl-1,2-benzenediol used as starting material is obtained from 28.2 g (226.7 mmol) of 4-methyl-1,2-benzenediol and 44.9 g (200 mmol) of 4-cyclohexylbenzenesulphinic acid (produced by reduction of the corresponding sulphonyl chloride with sodium sulphite) by oxidative condensation in a manner analogous to that described in Example 5a).

EXAMPLE 7

A suspension of 34.6 g (250 mmol) of freshly calcined potassium carbonate in 150 ml of dimethylformamide is stirred first with a high-speed stirrer for 5 minutes and then with a normal stirrer. A solution of 16.07 g (50 mmol) of 4-(3-acetamidophenylsulphonyl)-5-methyl-1,2-benzenediol in 50 ml of dimethylformamide is then added. After 5 minutes, a solution of 11.98 g (55 mmol) of dibromoacetic acid in 25 ml of dimethylformamide is added in the course of 15 minutes and this reaction mixture is heated for 4 hours at 80°. Water is then added and the whole is acidified with hydrochloric acid and filtered with suction. The filtrate is repeatedly extracted with ethyl acetate. The solid substance is dissolved in the combined organic phases and the solution is washed with water and saturated sodium chloride solution, dried over magnesium sulphate and concentrated at 60° until crystallisation begins. 5-(3-acetamidophenylsulphonyl)-6-methyl-1,3-benzodioxole-2-carboxylic acid is recrystallised from ethyl acetate, m.p. 186°–188°.

The required 4-(3-acetamidophenylsulphonyl)-5-methyl-1,2-benzenediol is obtained in a manner analogous to that described in Example 3a) from 29.7 g (150 mmol) of 3-acetamidobenzenesulphinic acid and 21.1 g (170 mmol) of 4-methyl-1,2-benzenediol by oxidative coupling; m.p. 220°–222° (from isopropanol/water).

EXAMPLE 8

In a manner analogous to that described in Example 4, the desired 5-(4-fluorophenylsulphonyl)-6-methyl-1,3-benzodioxole-2-carboxylic acid is obtained in the form of white crystals having a melting point of 157°–158.5° (from 1,2-dichloroethane) by condensation of 19.0 g (67.3 mmol) of 4-(4-fluorophenylsulphonyl)-5-methyl-1,2-benzenediol with 10.6 g (67.3 mmol) of dichloroacetic acid ethyl ester and 46.5 g (336.5 mmol) of potassium carbonate in 200 ml of 1,2-dimethoxyethane and subsequent hydrolysis with sodium hydroxide solution in methanol.

The required 4-(4-fluorophenylsulphonyl)-5-methyl-1,2-benzenediol is obtained in the form of yellow crystals having a melting point of 175°–177° (from acetonitrile) in a manner analogous to that described in Example 5a) by oxidative condensation of 31.6 g (197 mmol) of p-fluorobenzenesulphinic acid (produced either by reduction of the corresponding sulphonyl chloride with sodium sulphite or by Friedel-Crafts reaction of fluorobenzene and carbon disulphide) with 38.7 g (312 mmol) of 4-methyl-1,2-benzenediol.

EXAMPLE 9

A suspension of 72.8 g (526 mmol) of freshly calcined potassium carbonate in 300 ml of 1,2-dimethoxyethane is stirred under nitrogen for 10 minutes using a high-speed stirrer and then, while stirring normally, 37.0 g (105.3 mmol) of 4-(3-acetamido-4-methoxyphenylsulphonyl)-5-methyl-1,2-benzenediol, 16.5 g (105.3 mmol) of dichloroacetic acid ethyl ester and 3 g of tetrabutylammonium bromide are added. The mixture is boiled under reflux, 300 ml of acetone are added, the whole is boiled under reflux for 3 more hours, a further 60 g of potassium carbonate and 16.5 g of dichloroacetic acid ethyl ester are added, and the whole is boiled under reflux for 9 more hours. The reaction mixture is poured into water and acidified to pH 1–2 with hydrochloric acid. Some of the solvent is evaporated off in vacuo and the aqueous phase remaining is extracted with ethyl acetate. The combined organic phases are washed with water and saturated sodium chloride solution, dried over sodium sulphate and concentrated by evaporation in a rotary evaporator. The residue is recrystallised four times from acetonitrile, yielding 5-(3-acetamido-4-methoxyphenylsulphonyl)-6-methyl-1,3-benzodioxole-2-carboxylic acid in the form of white crystals having a melting point of 230° (sintering at 150°).

The required 4-(3-acetamido-4-methoxyphenylsulphonyl)-5-methyl-1,2-benzenediol is obtained in a manner analogous to that described in Example 5a) from 34.4 g (150 mmol) of 3-acetamido-4-methoxybenzenesulphinic acid and 211 g (170 mmol) of 4-methyl-1,2-benzenediol in the form of crystals having a melting point of 230°–232° (from isopropanol).

EXAMPLE 10

In a manner analogous to that described in Example 4, 30.0 g (111 mmol) of 4-methyl-5-(2-thienylsulphonyl)-1,2-benzenediol, 17.4 g (111 mmol) of dichloroacetic acid ethyl ester and 76.7 g (555 mmol) of potassium carbonate in 300 ml of 1,2-dimethoxyethane are boiled under reflux. After 18 hours, the reaction mixture is poured into water, stirred for one hour at room temperature and then adjusted to pH 1–2 by means of hydrochloric acid. Some of the 1,2-dimethoxyethane is distilled off in vacuo and the mixture remaining is extracted with ethyl acetate. The combined organic phases are washed with water and saturated sodium chloride solution, dried over sodium sulphate and concentrated by evaporation in a rotary evaporator. The resulting dark-red oil is chromatographed over silica gel. As eluant, a mixture of chloroform/methanol/concentrated ammonia in a ratio of 40:10:1 is used until elution of the starting diol, then an analogous mixture in a ratio of 12:5:1 is used. The uniform fractions are combined and concentrated almost completely by evaporation. Ice/water is added to the residue and the pH is adjusted to 1–2 with concentrated hydrochloric acid. The acidic solution is extracted with ethyl acetate. The combined organic phases are washed, dried and concentrated by evaporation. The residue is boiled in diisopropyl ether and the black sludge formed is removed by decanting. The clear solution is concentrated to a large extent and the substance which has crystallised out is filtered off with suction. The crystals are recrystallised from 1,2-dichloroethane, yielding 5-methyl-6-(2-thienylsulphonyl)-1,3-benzodioxole-2-carboxylic acid in the form of white crystals having a melting point of 162.5°–164.5°.

(a) The 4-methyl-5-(2-thienylsulphonyl)-1,2-benzenediol required as starting material is obtained in a manner analogous to that described in Example 5a) from 90 g (600 mmol) of 2-thiophenesulphinic acid (obtained by reduction of 2-thiophenesulphonyl chloride with sodium sulphite) and 84.5 g (681 mmol) of 4-methyl-1,2-benzenediol in the form of yellowish crystals having a melting point of 161°–163.5° (from ethyl acetate).

EXAMPLE 11

In a manner analogous to that described in Example 4, 21.3 g (64 mmol) of 4-(2,5-dichlorophenylsulphonyl)-5-methyl-1,2-benzenediol, 10.0 g (64 mmol) of dichloroacetic acid ethyl ester and 44.2 g (320 mmol) of potassium carbonate in 160 ml of 1,2-dimethoxyethane are boiled under reflux. After 18 hours, the reaction mixture is filtered and the solid filtration residue is washed twice with 1,2-dimethoxyethane. 44 g of fresh potassium carbonate and 10 g of dichloroacetic acid ethyl ester are added to the combined organic solutions and the whole is stirred for 5 minutes using a high-speed stirrer and boiled, while stirring normally, for a further 17 hours. Working up is carried out in a manner analogous to that described in Example 10. After drying carefully, 5-(2,5-dichlorophenylsulphonyl)-6-methyl-1,3-benzodioxole-2-carboxylic acid is obtained in the form of white crystals having a melting point of 155°–157° (from diisopropyl ether).

(a) The 4-(2,5-dichlorobenzenesulphonyl)-5-methyl-1,2-benzenediol used as starting material is obtained in the form of sand-coloured crystals having a melting point of 209.5°–212° (from acetonitrile) from 40 g (189.5 mmol) of 2,5-dichlorobenzenesulphinic acid (produced by reduction of 2,5-dichlorobenzenesulphochloride with sodium sulphite) and 26.7 g (215 mmol) of 4-methyl-1,2-benzenediol in a manner analogous to that described in Example 5a).

EXAMPLE 12

23 g (77 mmol) of 4-(2-chlorophenylsulphonyl)-5-methyl-1,2-benzenediol are added to a finely particulate suspension of 50.9 g (385 mmol) of freshly calcined potassium carbonate in 180 ml of dry dimethylformamide and there is added dropwise thereto, in the course of 15 minutes, a solution of 8.50 g (39 mmol) of dibromoacetic acid in 80 ml of dimethylformamide. The mixture is then stirred for 15 hours at 80°. Subsequently, the reaction mixture is poured onto ice and adjusted to pH 1–2 with concentrated hydrochloric acid. The aqueous phase is extracted once more with ethyl acetate. The combined organic phases are washed with water and saturated sodium chloride solution, dried with sodium sulphate and concentrated by evaporation. The resulting brown oil is stirred with 150 ml of ethyl acetate at 0° until crystallisation occurs. The crude 5-(2-chlorophenylsulphonyl)-6-methyl-1,3-benzodioxole-2-carboxylic acid so obtained is recrystallised twice from acetonitrile, resulting in the form of sand-coloured crystals having a melting point of 211°–213.5°.

(a) The 4-(2-chlorophenylsulphonyl)-5-methyl-1,2-benzenediol is obtained in the form of white crystals having a melting point of 225°–229° (from ethyl acetate) in a manner analogous to that described in Example 5a) from 26.5 g (150 mmol) of 2-chlorobenzenesulphinic acid and 21.1 g (170 mmol) of 4-methyl-1,2-benzenediol.

EXAMPLE 13

In a manner analogous to that described in Example 12, 5-(3-acetamido-4-chlorophenylsulphonyl)-6-methyl-1,3-benzodioxole-2-carboxylic acid is obtained by condensation of 22.0 g (61.8 mmol) of 4-(3-acetamido-4-chlorophenylsulphonyl)-5-methyl-1,2-benzenediol with 16.25 g (74.18 mmol) of dibromoacetic acid and 42.7 g (309 mmol) of potassium carbonate in 225 ml of dimethylformamide; m.p. 198°–200°.

Working up is carried out likewise in a manner analogous to that described in Example 12, by chromatographing the dark-red oil obtained as crude product over a silica gel funnel (chloroform/methanol/concentrated ammonia 40:10:1).

The uniform fractions are extracted with ethyl acetate, and the substance remaining after concentration by evaporation of the extract is recrystallised from acetonitrile, yielding the end product in the form of sand-coloured crystals having a melting point of 198°–200° (sinters from 120°).

The 4-(3-acetamido-4-chlorophenylsulphonyl)-5-methyl-1,2-benzenediol used as starting material is produced as follows:

(a) 66 g (297.8 mmol) of 4-chloro-3-nitrobenzenesulphinic acid (produced by reduction of 4-chloro-3-nitrobenzenesulphonyl chloride with sodium sulphite) are condensed with 41.95 g (337.9 mmol) of 4-methyl-1,2-benzenediol in a manner analogous to that described in Example 4, yielding 4-(4-chloro-3-nitrophenylsulphonyl)-5-methyl-1,2-benzenediol in the form of crystals having a melting point of 196°–197° (from ethyl acetate/hexane).

(b) 47.5 g (138.2 mmol) of the product obtained according to (a) are catalytically hydrogenated with hydrogen in the presence of Raney nickel to form 4-(3-amino-4-chlorophenylsulphonyl)-5-methyl-1,2-benzenediol. The latter is crystallised from 1,2-dichloroethane in the form of sand-coloured crystals having a melting point of 191°–193°.

(c) 40 g (112.42 mmol) of the amine obtained according to (b) are acetylated with 11.48 g (112.42 mmol) of acetic anhydride in 240 ml of glacial acetic acid to form the desired 4-(3-acetamido-4-chlorophenylsulphonyl)-5-methyl-1,2-benzenediol, which is obtained from acetonitrile in the form of white crystals having a melting point of 224°–226.5°.

EXAMPLE 14

21.0 g (70.3 mmol) of 4-chloro-5-(4-methylphenylsulphonyl)-1,2-benzenediol and 48.6 g (approximately 350 mmol) of anhydrous pulverised potassium carbonate are suspensed in 160 ml of dimethylformamide at room temperature under inert gas. A solution of 16.8 g (77.4 mmol) of dibromoacetic acid in 80 ml of dimethylformamide is then added dropwise thereto at room temperature, while stirring, in the course of 15 minutes. The reaction mixture is then heated for 15 hours at 95° while stirring. For working up, the reaction mixture is poured onto an ice/water mixture and acidified with concentrated hydrochloric acid to pH 2. The crude product is extracted with ethyl acetate and the solvent is evaporated off. The crude acid remaining is dissolved in 100 ml of methanol, and 0.5 ml of concentrated hydrochloric acid is added. After standing for 5 hours at room temperature, crystallisation commences. The crystal suspension is cooled in an ice bath for 18 hours, then the crystals are filtered off and washed with ice-cold methanol. They are then suspended in 60 ml of methanol, and 35 ml of 2N sodium hydroxide solution are added at room temperature, a solution being formed. After being left to stand for one hour, the solution is poured out onto an ice/water mixture and acidified with 6N hydrochloric acid. The 5-chloro-6-(4-methylphenylsulphonyl)-1,3-benzodioxole-2-carboxylic acid precipitates and is extracted with ethyl acetate. The residue of the extract, obtained by concentration by evaporation, is recrystallised from acetonitrile, and in this manner the above substance is obtained in the form of sand-coloured crystals having a melting point of 181°–183.5°.

The aromatic starting material is produced as follows:

(a) In a manner analogous to that described in Example 5a), p-toluenesulphinic acid is oxidatively condensed with 4-chloro-1,2-benzenediol. On recrystallisation from 1,2-dichloroethane, 4-chloro-(4-methylphenylsulphonyl)-1,2-benzenediol is obtained in the form of colourless crystals having a melting point of 162°–164°.

EXAMPLE 15

42.6 g (approximately 0.13 mol) of 4-bromo-5-(phenylsulphonyl)-1,2-benzenediol and 90.0 g (approximately 0.65 mol) of anhydrous pulverised potassium carbonate are stirred in 300 ml of dimethylformamide under inert gas protection. At room temperature, half of a solution of 57.0 g (approximately 0.26 mol) of dibromoacetic acid in 100 ml of dimethylformamide is added. The reaction mixture is stirred for 8 hours at 95°, then the remainder of the dibromoacetic acid solution is added and the whole is stirred for a further 8 hours at 95°. Subsequently, the dimethylformamide is distilled off at reduced pressure, the residue is dissolved in water, the solution is adjusted to pH 1–2 with concentrated hydrochloric acid and extraction is carried out with ethyl acetate. The ethyl acetate solution is washed with water, dried over sodium sulphate and concentrated by evaporation. The residue is dissolved in 150 ml of methanol, and 0.3 ml of concentrated hydrochloric acid is added. After being left to stand overnight at room temperature, the solution is concentrated by evaporation and the residue is chromatographed on a column of silica gel with the eluant mixture ethyl acetate/hexane 1:2. The uniform fractions are combined and concentrated by evaporation. 50 ml of 2N sodium hydroxide solution are added to the residue obtained by concentration by evaporation, and the whole is stirred at room temperature with a magnetic stirrer until a solution has formed. This solution is adjusted to pH 1–2 with concentrated hydrochloric acid and the precipitated acid is repeatedly extracted with ethyl acetate. The combined ethyl acetate solutions are washed with water, dried with sodium sulphate, filtered and concentrated by evaporation, resulting in 5-bromo-6-(phenylsulphonyl)-1,3-benzodioxole-2-carboxylic acid in the form of a white crystalline crust. Recrystallisation from ethyl acetate/hexane yields the above substance in the form of colourless crystals having a melting point of 219°–222° (decomposition).

The aromatic starting material is obtained in the following manner:

(a) 48.0 g of 4-bromo-1,2-benzenediol [cf. W. Rosermund, Ber. 62, 1262 and so forth (1923)] are oxidatively condensed with 33.4 g of the sodium salt of benzenesulphinic acid in a manner analogous to that described in Example 5a). Crystallisation from 1,2-dichloroethane yields 4-bromo-5-(phenylsulphonyl)-1,2-benzenediol in the form of colourless crystals having a melting point of 166°–168°.

EXAMPLE 16

25.0 g (approximately 85 mmol) of 4-(4-methoxyphenylsulphonyl)-5-methyl-1,2-benzenediol are reacted in 200 ml of dimethylformamide, using 60 g of potassium carbonate, with 20.4 g (93.5 mmol) of dibromoacetic acid in 100 ml of dimethylformamide, in a manner entirely analogous to that described in Example 14. The resulting crude acid is dissolved in ethyl acetate, and a solution of 5.8 g of the sodium salt of hexanoic acid in methanol is added. The resulting crystals are filtered off and dried. In this manner the sodium salt of 5-(4-methoxyphenylsulphonyl)-6-methyl-1,3-benzodioxole-2-carboxylic acid is obtained in the form of colourless crystals having a melting point of above 220° (decomposition).

The aromatic starting material is obtained as follows:

(a) 37.5 g of 4-methoxybenzenesulphinic acid (obtained, for example, by reduction of 4-methoxybenzenesulphonyl chloride with sodium sulphite) are condensed oxidatively with 30.7 g of 4-methyl-1,2-benzenediol in a manner analogous to that described in Example 5a) and, after crystallisation from 1,2-dichloroethane, 4-(4-methoxyphenylsulphonyl)-5-methyl-1,2-benzenediol is obtained in the form of colourless crystals having a melting point of 145°–147.5°.

EXAMPLE 17

15.0 g (0.05 mol) of 4-(2,4-difluorobenzenesulphonyl)-5-methyl-1,2-benzenediol and 34.6 g (0.25 mol) of potassium carbonate are suspended at room temperature under nitrogen protection in 100 ml of dimethylformamide. In the course of 10 minutes, a solution of 11.9 g (approximately 0.055 mol) of dibromoacetic acid in 30 ml of dimethylformamide is added dropwise and the reaction mixture is then heated at 90° for 5½ hours while stirring. The reaction mixture is poured into 1500 ml of water and adjusted to pH 1–2 with concentrated hydrochloric acid. The crude acid is extracted with ethyl acetate, and the ethyl acetate solution is washed with water, dried over sodium sulphate, filtered and concentrated by evaporation. 50 ml of 1N sodium hydroxide solution are added to the residue obtained by concentration by evaporation, and the resulting solution is concentrated by evaporation in a rotary evaporator until the sodium salt begins to crystallise out. By the addition of isopropanol and heating to reflux a solution is obtained again, activated carbon is added and the whole is filtered. On cooling the filtrate, the sodium salt of 5-(2,4-difluorophenylsulphonyl)-6-methyl-1,3-benzodioxole-2-carboxylic acid is precipitated in the form of colourless needles. After filtration and drying, the salt melts at a temperature of above 200°, after sintering from 160°.

The starting material is produced as follows:

(a) By Meerwein reaction using 2,4-difluoroaniline as starting material, 2,4-difluorobenzenesulphonyl chloride, b.p.: 87°/5 mbar, is obtained.

(b) By reduction of 2,4-difluorobenzenesulphonyl chloride with sodium sulphite, 2,4-difluorobenzenesulphinic acid is obtained.

(c) In a manner analogous to that described in Example 5a), there is obtained by oxidative condensation of 23.5 g of 2,4-difluorobenzenesulphinic acid with 18.5 g of 4-methyl-1,2-benzenediol, after recrystallisation from 1,2-dichloroethane, 4-(2,4-difluorobenzenesulphonyl)-5-methyl-1,2-benzenediol having a melting point of 158°–162°.

EXAMPLE 18

In a manner analogous to that described in Example 1, 18.3 g of 4-(3-chloro-4-fluorophenylsulphonyl)-5-methyl-1,2-benzenediol is reacted in the presence of 39.9 g of potassium carbonate with 10.0 g of dichloroacetic acid ethyl ester in 150 ml of dimethoxyethane. There is obtained, after analogous working up and recrystallisation from acetonitrile, 5-(3-chloro-4-fluorophenylsulphonyl)-6-methyl-1,3-benzodioxole-2-carboxylic acid in the form of colourless crystals having a melting point of 188.5°–190.5°.

The aromatic starting material is produced as follows:

(a) The 3-chloro-4-fluorobenzenesulphochloride used in Example 18b, b.p. 90°–95°/5 mbar, is obtained according to processes known in the literature, for example by Meerwein reaction from 3-chloro-4-fluoroaniline.

(b) By reduction of 3-chloro-4-fluorobenzenesulphochloride with sodium sulphite, 3-chloro-4-fluorobenzenesulphinic acid having a melting point of 66°–68° is obtained.

(c) There is obtained in a manner analogous to that described in Example 5a), by oxidative condensation of 3-chloro-4-fluorobenzenesulphinic acid with 4-methyl-1,2-benzenediol, the 4-(3-chloro-4-fluorophenylsulphonyl)-5-methyl-1,2-benzenediol used in the above Example 18 having a melting point of 166°–167.5° in the form of colourless crystals.

EXAMPLE 19

In a manner analogous to that described in Example 17, 14 g (42.8 mmol) of 5-(4-chloro-2,5-dimethylphenylsulphonyl)-4-methyl-1,2-benzenediol and 10.3 g of dibromoacetic acid are reacted in the presence of 29.6 g of potassium carbonate in 150 ml of dimethylformamide and, after working up, salt formation with sodium hydroxide solution and recrystallisation from isopropanol/water, there is obtained the sodium salt of 5-(4-chloro-2,5-dimethylphenylsulphonyl)-6-methyl-1,3-benzodioxole-2-carboxylic acid in the form of colourless crystals having a melting point of >180° (decomposition).

The 5-(4-chloro-2,5-dimethylphenylsulphonyl)-4-methyl-1,2-benzenediol used as starting material is obtained by oxidative condensation of 4-chloro-2,5-dimethylbenzenesulphonic acid (in turn obtained by reduction of 4-chloro-2,5-dimethylbenzenesulphochloride with sodium sulphite) with 4-methyl-1,2-benzenediol in a manner analogous to that described in Example 5a) and crystallisation from ethyl acetate, in the form of yellowish crystals having a melting point of 193°–196°. (sintering from 143°).

EXAMPLE 20

31.2 g (0.1 mol) of 5-(4-chloro-2,5-dimethylphenylsulphonyl)-4-methyl-1,2-benzenediol and 55 g (0.4 mol) of potassium carbonate are suspended in 150 ml of dimethylformamide under an inert gas. At room temperature 17.3 g (0.11 mol) of dichloroacetic acid ethyl ester are added and the mixture is then heated at 80° for 10 hours. For working up, the dimethylformamide is distilled off in vacuo and the residue is dissolved in water. The solution is acidified to pH 1–2 with concentrated hydrochloric acid and the precipitated crude acid is repeatedly extracted with ethyl acetate. The combined ethyl acetate solutions are concentrated by evaporation and the residue is dissolved at elevated temperature in the equivalent amount of 2N sodium hydroxide solution. On cooling, the sodium salt of 5-(4-chloro-2,5-dimethylphenylsulphonyl)-6-methyl-1,3-benzodioxole-2-carboxylic acid precipitates. After cooling, it is filtered off and recrystallised from isopropanol in the manner described in Example 19.

EXAMPLE 21

In a manner analogous to that described in Example 17, 25 g (71.7 mmol) of 4-(2,4-dichloro-5-methylphenylsulphonyl)-5-methyl-1,2-benzenediol are reacted with 17.14 g (78.7 mmol) of dibromoacetic acid in the presence of 49.5 g of potassium carbonate in 250 ml of dimethylformamide. After working up, salt formation and recrystallisation in a manner analogous to that described in Example 17, the sodium salt of 5-(2,4-dichloro-5-methylphenylsulphonyl)-6-methyl-1,3-benzodioxole-2-carboxylic acid is obtained in the form of colourless crystals having a melting point of 200° (decomposition).

(a) The 4-(2,4-dichloro-5-methylphenylsulphonyl)-5-methyl-1,2-benzenediol used above is obtained by oxidative condensation of 2,4-dichloro-5-methylbenzenesulphinic acid (obtained from 2,4-dichloro-5-methylbenzenesulphochloride by reduction with Na-sulphite) with 4-methyl-1,2-benzenediol in a manner analogous to that described in Example 5a); m.p. 203.5°–206° (decomposition, from acetonitrile).

EXAMPLE 22

In a manner analogous to that described in Example 15, 60.0 g of 4-(4-bromophenylsulphonyl)-5-methyl-1,2-benzenediol are reacted in the presence of 120 g of potassium carbonate in 300 ml of dimethylformamide with a solution of 76.2 g of dibromoacetic acid in 100 ml of dimethylformamide. After working up and chromatographic purification in a manner analogous to that described in Example 15 and crystallisation from 1,2-dichloroethane, 5-(4-bromophenylsulphonyl)-6-methyl-1,3-benzodioxole-2-carboxylic acid is obtained in the form of sand-coloured crystals having a melting point of 170°–172.5°.

(a) The 4-(4-bromophenylsulphonyl)-5-methyl-1,2-benzenediol used in the above Example is obtained by oxidative condensation of 76.0 g of p-bromobenzenesulphinic acid (obtained from p-bromobenzenesulphochloride by reduction with sodium sulphite) with 53.0 g of 4-methyl-1,2-benzenediol in a manner analogous to that described in Example 5a), in the form of colourless crystals having a melting point of 190°–191.5° (from chloroform).

EXAMPLE 23

39.6 g (approximately 0.105 mol) of 4-[(2-tert.butyl-6-benzothiazolyl)-sulphonyl]-5-methyl-1,2-benzenediol and 72.3 g (0.523 mol) of potassium carbonate are stirred in 300 ml of dimethylformamide at room temperature under inert gas protection. In the course of 20 minutes there is added dropwise thereto half of a solution of 45.6 g (0.209 mol) of dibromoacetic acid in 100 ml of dimethylformamide. The reaction mixture is subsequently stirred for 21 hours at 100° and, during this time, the remainder of the dibromoacetic acid solution is added in small portions. For working up, the dimethylformamide is distilled off in a rotary evaporator under a water jet vacuum. The residue is dissoled in water and adjusted to pH 1–2 with concentrated hydrochloric acid. The precipitated acid is extracted three times with ethyl acetate. The combined ethyl acetate solutions are washed once with water, dried over sodium sulphate, filtered and concentrated by evaporation. The residue is dissolved in 500 ml of ethanol, and after the addition of 0.5 ml of concentrated hydrochloric acid the solution is left to stand at room temperature for 10 days. During this time, the ethyl ester of 5-methyl-6-[(2-tert.-butyl-6-benzothiazolyl)-sulphonyl]-1,3-benzodioxole-2-carboxylic acid is precipitated in the form of colourless crystals. The crystal suspension is cooled to 0° and the crystals are filtered off. 90 ml of 2N sodium hydroxide solution are added to the crystals, still moist with ethanol, and the mixture is stirred for 2 hours at room temperature, a solution being formed. This is acidified with concentrated hydrochloric acid and the precipitated acid is extracted three times with ethyl acetate. The ethyl acetate solutions are washed with water, dried over sodium sulphate, filtered and concentrated by evaporation in vacuo to dryness. The residue is recrystallised from ethyl acetate, yielding 5-methyl-6-[(2-tert.-butyl-6-benzothiazolyl)-sulphonyl]-1,3-benzodioxole-2-carboxylic acid in the form of colourless crystals having a melting point of 247° (decomposition), after sintering from 203°.

The starting material is produced as follows:

(a) 2-Tert.-butyl-6-benzothiazolesulphochloride is obtained by the known Meerwein reaction, using as starting material 6-amino-2-tert.-butylbenzothiazole.

(b) By reduction of 2-tert.-butyl-6-benzothiazolesulphochloride, 2-tert.-butylbenzothiazole-2-sulphinic acid, which melts at a temperature of above 150°, is obtained.

(c) 4-Methyl-5-[(2-tert.-butyl-6-benzothiazolyl)sulphonyl]-1,2-benzenediol having a melting point of 185° (decomposition) is obtained in a manner analogous to that described in Example 5a) with subsequent chromatography.

EXAMPLE 24

In a manner analogous to that described in Example 15, corresponding amounts of 4-chloro-5-phenylsulphonyl-1,2-benzenediol and dibromoacetic acid in dimethylformamide are reacted in the presence of potassium carbonate. After working up, purification and recrystallisation in a manner analogous to that described in Example 15, 5-chloro-6-phenylsulphonyl-1,3-benzodioxole-2-carboxylic acid having a melting point of 183°–185° is obtained.

(a) The 4-chloro-5-phenylsulphonyl-1,2-benzenediol used in the above Example is obtained by reaction of benzenesulphinic acid with 4-chloro-1,2-benzenediol in a manner analogous to that described in Example (5a); m.p. 161°–165°.

EXAMPLE 25

In a manner analogous to that described in Example 15, there is obtained by reaction of corresponding amounts of 4-chloro-5-(4-chlorophenylsulphonyl)-1,2-benzenediol and dibromoacetic acid in dimethylformamide in the presence of potassium carbonate and by analogous working up, purification and recrystallisation, 5-chloro-6-(4-chlorophenylsulphonyl)-1,3-benzodioxole-2-carboxylic acid having a melting point of 194°–196°.

(a) The 4-chloro-5-(4-chlorophenylsulphonyl)-1,2-benzenediol used in the above Example is obtained by reaction of 4-chlorobenzenesulphinic acid and 4-chloro-1,2-benzenediol in a manner analogous to that described in Example (5a); m.p. 165°–176°.

EXAMPLE 26

In a manner analogous to that described in Example 14, 20.1 g of 4-(4-acetylphenylsulphonyl)-5-methyl-1,2-benzenediol and 28.3 g of dibromoacetic acid are reacted in 130 ml of dimethylformamide in the presence of 45 g of potassium carbonate. After analogous working up and purification, 5-(4-acetylphenylsulphonyl)-6-methyl-1,3-benzodioxole-2-carboxylic acid having a melting point of 107°–110° is obtained.

The aromatic starting material is produced as follows:

(a) By the reduction of 4-acetylbenzenesulphonyl chloride with sodium sulphite, 4-acetylbenzenesulphinic acid is obtained.

(b) By oxidative condensation of 4-acetylbenzenesulphinic acid with 4-methyl-1,2-benzenediol, 4-(4-acetylphenylsulphonyl)-5-methyl-1,2-benzenediol having a melting point of 184°–188° is obtained.

EXAMPLE 27

10.0 g (0.0359 mol) of 4-phenylsulphonyl-5-ethyl-1,2-benzenediol and 31.5 (0.288 mol) of potassium carbonate are placed in 100 ml of dimethylformamide at room temperature under inert gas protection, and 9.0 g (0.0413 mol) of dibromoacetic acid are added. The reaction mixture is maintained at an internal temperature of approximately 80° for 14 hours while stirring. Subsequently, the dimethylformamide is distilled off in a rotary evaporator under a water jet vacuum, and the residue is taken up in water. The pH is adjusted to 1–2 with concentrated HCl, the crude acid is extracted with ethyl acetate, and the extract is dried with sodium sulphate, filtered and concentrated to dryness by evaporation in a rotary evaporator. The residue is dissolved in 100 ml of absolute ethanol, 0.2 ml of concentrated HCl are added and the whole is boiled at reflux for two hours. It is then concentrated to dryness by evaporation, the residue is taken up in ethyl acetate and washed in a separating funnel once with saturated sodium bicarbonate solution and twice with water. The ethyl acetate phase is dried over sodium sulphate, filtered and concentrated by evaporation. 20 ml of 2N NaOH are added to the residue and the whole is heated on a warm water bath until a yellowish solution has formed. The solution is cooled, adjusted to pH 1–2 with concentrated HCl, and the purified 5-phenylsulphonyl-6-ethyl-1,3-benzodioxole-2-carboxylic acid is extracted with ethyl acetate. The extract solution is dried over sodium sulphate and filtered. 50 ml of toluene are added and the ethyl acetate is evaporated off in a rotary evaporator. The acid is precipitated in the form of colourless crystals having a melting point of 143°–145°.

(a) The 4-phenylsulphonyl-5-ethyl-1,2-benzenediol used in the above Example is obtained by oxidative coupling of benzenesulphinic acid with 4-ethyl-1,2-benzenediol in a manner analogous to that described in Example 1a); m.p. 180°–182°.

EXAMPLE 28

27.5 g (0.097 mol) of 4-(2-methylphenylsulphonyl)-5-methyl-1,2-benzenediol, 62.1 g (0.45 mol) of potassium carbonate and 32.7 g (0.145 mol) of dibromoacetic acid (97% strength) are reacted in 300 ml of dimethylformamide under an inert gas atmosphere in a manner analogous to that described in Example 27. After working up, purification by way of the ethyl ester and hydrolysis, in a manner entirely analogous to that described in Example 27, 5-(2-methylphenylsulphonyl)-6-methyl-1,3-benzodioxole-2-carboxylic acid is obtained in the form of colourless crystals having a melting point of 178°–180° (from toluene).

The 4-(2-methylphenylsulphonyl)-5-methyl-1,2-benzenediol used above is produced as follows:

(a) 33.2 g (0.108 mol) of 1,2-dimethoxy-4-(2-methylphenylsulphonyl)-5-methylbenzene and 70 g (0.6 mol) of pyridine hydrochloride are heated together in a bath of 200° for 2½ hours to form a melt. The melt is poured onto ice, 20 ml of concentrated HCl are added and extraction with ethyl acetate is then carried out. The extract solution is washed twice with water, dried with sodium sulphate, filtered and concentrated in a rotary evaporator. When a volume of approximately 100 ml has been reached, the product begins to crystallise out. The whole is cooled for ½ hour in an ice bath, filtered, and the resulting beige crystals of 4-(2-methylphenylsulphonyl)-5-methyl-1,2-benzenediol having a melting point of 221°–223° are dried.

The starting material used in Example 28a) is obtained in the following manner:

(b) 50 g of phosphorus pentoxide are covered, by pouring, with 400 ml of methanesulphonic acid and the whole is stirred at 60° until a clear solution has formed. 30.4 g (0.2 mol) of 1,2-dimethoxy-4-methylbenzene and 43 g (0.2 mol) of 2-methylbenzenesulphonic acid (80% strength) are then added, and the internal temperature is increased to 80° for 30 minutes. The mixture is poured onto 4 liters of ice-water and extracted with ethyl acetate. The extract solution is washed twice with water, dried over sodium sulphate, filtered and concentrated by evaporation in a rotary evaporator. The oil remaining crystallises immediately. It is triturated with diethyl ether and filtered off. In this manner colourless crystals of 1,2-dimethoxy-4-(2-methylphenylsulphonyl)-5-methylbenzene having a melting point of 126°–128° are obtained.

EXAMPLE 29

24.5 g (0.088 mol) of 4-(3-methylphenylsulphonyl)-1,2-benzenediol, 60.7 g (0.44 mol) of potassium carbonate and 29.6 g (0.132 mol) of dibromoacetic acid (97% strength) are reacted in 300 ml of dimethylformamide in a manner analogous to that described in Example 27. After working up, purification by way of the ethyl ester and hydrolysis in a manner analogous to that described in Example 27, colourless crystals of 5-(3-methylphenylsulphonyl)-6-methyl-1,3-benzodioxole-2-carboxylic acid having a melting point of 155°–157° are obtained from toluene/ethyl acetate.

(a) The 4-(3-methylphenylsulphonyl)-1,2-benzenediol used above as produced in a manner analogous to that described in Example 28a) by ether cleaving of 1,2-dimethoxy-4-(3-methylphenylsulphonyl)-5-methylbenzene by means of pyridine/hydrochloride; m.p. 172°–174° (from toluene/ethyl acetate).

(b) The above 1,2-dimethoxy-4-(3-methylphenylsulphonyl)-5-methylbenzene is obtained by reacting 3-methylbenzenesulphonic acid with 1,2-dimethoxy-4-methylbenzene in a manner analogous to that described in Example (28b); m.p. 135°–140° (from ether).

EXAMPLE 30

13.1 g (0.0438 mol) of 4-(3-chlorophenylsulphonyl)-5-methyl-1,2-benzenediol, 30.0 g (0.217 mol) of potassium carbonate and 14.7 g (0.065 mol) of dibromoacetic acid (97% strength) are stirred in 150 ml of dimethylformamide for 5 hours at an internal temperature of 80° under an inert gas atmosphere. After working up, purification by way of the ethyl ester and hydrolysis in a manner analogous to that described in Example 27, colourless crystals of 5-(3-chlorophenylsulphonyl)-6-methyl-1,3-benzodioxole-2-carboxylic acid having a melting point of 172°–174° (from toluene/ethyl acetate) are obtained.

(a) The 4-(3-chlorophenylsulphonyl)-5-methyl-1,2-benzenediol used above is obtained in a manner analogous to that described in Example 28a) by ether cleaving from 1,2-dimethoxy-4-(3-chlorophenylsulphonyl)-5-methylbenzene by means of pyridine hydrochloride; m.p. 185°–187° (from toluene/ethyl acetate).

(b) The 1,2-dimethoxy-4-(3-chlorophenylsulphonyl)-5-methylbenzene used in Example 30a) is obtained in a manner analogous to that described in Example 28b) by condensation of 3-chlorobenzenesulphonic acid with 1,2-dimethoxy-4-methylbenzene in phosphorus pentoxide/methanesulphonic acid while heating for one hour at 80°; m.p. 151°–152° (from toluene).

EXAMPLE 31

9.2 g (0.029 mol) of 4-chloro-5-(3-chlorophenylsulphonyl)-1,2-benzenediol, 18.0 g (0.13 mol) of potassium carbonate and 9.5 g (0.042 mol) of dibromoacetic acid (97% strength) are reacted in 70 ml of dimethylformamide in a manner analogous to that described in Example 27. After working up and esterifyng in a manner analogous to that described in Example 27, the crude ester is chromatographed over 200 g of silica gel with the solvent mixture hexane/ethyl acetate (9:1), and the uniform fractions are combined, concentrated by evaporation and then hydrolysed with 2N NaOH. After liberation and isolation of the 5-chloro-6-(3-chlorophenylsulphonyl)-1,3-benzodioxole-2-carboxylic acid, this is re-crystallised from toluene/ethyl acetate; m.p. 182°–184°.

The 4-chloro-5-(3-chlorophenylsulphonyl)-1,2-benzenediol used above can be produced in the following manners:

(a) By oxidative coupling of 3-chlorobenzenesulphinic acid with 4-chloro-1,2-benzenediol in a manner analogous to that described in Example (3a) there is obtained, after crystallisation from toluene/ethyl acetate, 4-chloro-5-(3-chlorophenylsulphonyl)-1,2-benzenediol having a melting point of 192°–194°.

(b) 4-chloro-5-(3-chlorophenylsulphonyl)-1,2-benzenediol is also obtained by ether cleaving 1,2-dimethoxy-4-chloro-5-(3-chlorophenylsulphonyl)-benzene by means of pyridine hydrochloride in a manner analogous to that described in Example 28a).

(c) The 1,2-dimethoxy-4-chloro-5-(3-chlorophenylsulphonyl)-benzene used in Example 31b) is obtained by reacting 3-chlorobenzenesulphonic acid with 1,2-dimethoxy-4-chlorobenzene in a manner analogous to that described in Example 28b); m.p. 154°–156°.

EXAMPLE 32

19.7 g (0.065 mol) of 4-chloro-5-(4-fluorophenylsulphonyl)-1,2-benzenediol, 40.1 g (0.29 mol) of potassium carbonate and 23.6 g (0.108 mol) of dibromoacetic acid (97% strength) are stirred in 160 ml of dimethylformamide for 20 hours at 80° under an inert gas atmosphere. The dimethylformamide is evaporated off in a rotary evaporator under a water jet vacuum and the residue is taken up in water. The pH is adjusted to 1–2 with concentrated HCl, then extraction is carried out with ethyl acetate. The extract solution is concentrated by evaporation and the residue is dissolved in 250 ml of absolute ethanol. After the addition of 0.2 ml of concentrated HCl, the whole is boiled at reflux for 2 hours and then concentrated to dryness by evaporation. The resinous residue is chromatographed over 400 g of silica gel with a solvent mixture of chloroform/hexane/ethyl acetate (1:1:1). The uniform fractions are collected and concentrated by evaporation. 100 ml of 2N NaOH are added to the resulting ethyl ester of 5-chloro-6-(4-fluorophenylsulphonyl)-1,3-benzodioxole-2-carboxylic acid and the whole is stirred for one hour at 80°. At elevated temperature, activated carbon is added to the resulting yellow solution and filtration is carried out. On cooling, the sodium salt of 5-chloro-6-(4-fluorophenylsulphonyl)-1,3-benzodioxole-2-carboxylic acid crystallises into fine colourless flakes; m.p. 216°–220° (decomposition).

(a) The 4-chloro-5-(4-fluorophenylsulphonyl)-1,2-benzenediol used above is obtained in a manner analogous to that described in Example 3a) by oxidative coupling of 4-chloro-1,2-benzenediol with 4-fluorobenzenesulphinic acid; m.p. 180°–182° (from ethyl acetate/toluene).

EXAMPLE 33

18.1 g (0.05 mol) of 4-chloro-5-(4-bromophenylsulphonyl)-1,2-benzenediol, 31.0 g (0.244 mol) of potassium carbonate and 18.4 g (0.083 mol) of dibromoacetic acid (97% strength) are reacted in 120 ml of dimethylformamide in a manner analogous to that described in Example 27. After working up, purification by way of the ethyl ester and hydrolysis entirely analogously to Example 27, 5.8 g of 5-chloro-6-(4-bromophenylsulphonyl)-1,3-benzodioxole-2-carboxylic acid having a melting point of 193°–196° (from toluene) are obtained.

(a) The 4-chloro-5-(4-bromophenylsulphonyl)-1,2-benzenediol used above is obtained by oxidative coupling of 4-bromobenzenesulphinic acid with 4-chloro-1,2-benzenediol in a manner analogous to that described in Example 3a); m.p. 183°–187°.

EXAMPLE 34

12.3 g (0.037 mol) of 5-phenylsulphinyl-6-methyl-1,3-benzodioxole-2-carboxylic acid ethyl ester are heated with 20 ml of 2N NaOH for ½ hour at 60°–70°. The mixture is cooled, adjusted to pH 1–2 with 2N HCl and extracted with ethyl acetate. The extract solution is washed with water, dried over sodium sulphate, filtered and concentrated by evaporation. The crystalline residue of 10 g is dissolved at elevated temperature with 300 ml of ethyl acetate and 50 ml of acetone, activated carbon is added and the whole is filtered. The filtrate is concentrated to 100 ml in a rotary evaporator. Beige-coloured crystals of 5-phenylsulphinyl-6-methyl-1,3-benzodioxole-2-carboxylic acid having a melting point of from 170° (decomposition) are thereby precipitated.

The ethyl ester used above is produced in the following manner:

(a) 20.8 g (0.1 mol) of 5-methyl-1,3-benzodioxole-2-carboxylic acid ethyl ester Example 2b) and 19.2 g (0.125 mol) of phenylsulphinic acid chloride are dissolved in 200 ml of 1,2-dichloroethane and cooled to 5° using an ice-bath. 13.3 g (0.1 mol) of aluminium chloride are introduced in the course of approximately 15 minutes at from 5°–10° while stirring. The mixture is stirred for a further hour in the ice-bath and is then poured out onto ice-water. The resulting emulsion is diluted with 200 ml of dichloroethane and filtered across a layer of a filter aid (for example Hyflo). The filtrate is introduced into a separating funnel and the layers are separated. The organic phase is dried over sodium sulphate, filtered and concentrated to dryness by evaporation. A light brown honey-like product, 5-phenylsulphinyl-6-methyl-1,3-benzodioxole-2-carboxylic acid ethyl ester, is obtained.

EXAMPLE 35

250 ml of absolute ethanol and 0.2 ml of concentrated HCl are added to 24.4 g (0.065 mol) of 5-chloro-6-(4-chlorophenylsulphonyl)-1,3-benzodioxole-2-carboxylic acid (obtained according to Example 25) and the whole is boiled at reflux for ½ hour. 100 ml of ethanol are distilled off and there crystallises from the remaining solution, on cooling, 5-chloro-6-(4-chlorophenylsulphonyl)-1,3-benzodioxole-2-carboxylic acid ethyl ester in the form of coarse colourless crystals; m.p. 122°–123°.

EXAMPLE 36

3.88 g (0.0069 mol) of 5-chloro-6-(4-chlorophenylsulphonyl)-1,3-benzodioxole-2-carboxylic acid ethyl ester are dissolved in 20 ml of dimethylformamide and are added to 0.71 g (0.012 mol) of guanidine at room temperature. The mixture is stirred for 2 hours at room temperature, then poured out onto 200 ml of water. After stirring for ½ hour, a crystalline suspension has formed. This is filtered, washed with water, and the crude product is dried in a vacuum drying chamber at 30°–40°. The crude product is then digested with 25 ml of ethyl acetate, partial dissolution and recrystallisation occurring. The whole is cooled for ½ hour in an ice-bath, filtered and dried, yielding, in the form of beige crystals, 5-chloro-6-(4-chlorophenylsulphonyl)-1,3-benzodioxole-2-carboxylic acid guanidide having a melting point of from 215° (decomposition).

EXAMPLE 37

4.03 mol of 5-chloro-6-(4-chlorophenylsulphonyl)-1,3-benzodioxole-2-carboxylic acid ethyl ester are dissolved in room temperature in 50 ml of dichloromethane. While stirring vigorously, 50 ml of a concentrated aqueous ammonia solution are added, and stirring is continued for 18 hours. A thick crystalline suspension is formed from the initial emulsion. This suspension is then adjusted by 6N HCl to pH 2–3 at room temperature, filtered and subsequently washed with water. After drying, colourless crystals of 5-chloro-6-(4-chlorophenylsulphonyl)-1,3-benzodioxole-2-carboxylic acid amide having a melting point of 240°–242° are obtained.

EXAMPLE 38

34.8 g (0.1 mol) of 5-phenylsulphonyl-6-methyl-1,3-benzodioxole-2-carboxylic acid ethyl ester (from Example 2) are dissolved in 350 ml of dioxan (absolute) and treated in a pressure autoclave with approximately 20 g of ammonia gas. The reaction mixture is heated for 10 hours at 80° in the autoclave, the pressure is released, and the solution is concentrated to dryness by evaporation under reduced pressure. The residue is recrystallised from 120 ml of ethanol, yielding colourless crystals of 5-phenylsulphonyl-6-methyl-1,3-benzodioxole-2-carboxylic acid amide having a melting point of 138°–141°.

EXAMPLE 39

Tablets containing 50 mg of 5-methyl-6-phenylsulphonyl-1,3-benzodioxole-2-carboxylic acid can be manufactured, for example, in the following composition:

| Composition | per tablet |
| --- | --- |
| 5-methyl-6-phenylsulphonyl-1,3-benzodioxole-2-carboxylic acid | 50 mg |
| lactose | 50 mg |
| wheat starch | 73 mg |
| colloidal silica | 13 mg |
| talc | 12 mg |
| magnesium stearate | 2 mg |
| | 200 mg |

MANUFACTURE

The active ingredient is mixed with lactose, a portion of the wheat starch and with colloidal silica and the mixture is forced through a sieve. A further portion of the wheat starch is made into a paste on a water bath with 5 times the amount of water, and the powder mixture is kneaded with this paste until a slightly plastic mass is formed. The mass is forced through a sieve having a mesh width of approximately 3 mm, dried, and the dry granulate is forced through a sieve again. The remainder of the wheat starch, the talc and the magnesium stearate are then admixed. The resulting mixture is pressed to form tablets each of 250 mg with (a) breaking notch (es).

EXAMPLE 40

To produce 1000 capsules each containing 50 mg of active ingredient, 50.0 g of 5-methyl-6-phenylsulphonyl-1,3-benzodioxole-2-carboxylic acid are mixed with 223.0 g of lactose, the mixture is uniformly moistened with an aqueous solution of 2.0 g of gelatin and granulated by means of a suitable sieve (for example sieve III according to Ph. Helv. V.). The granulate is mixed with 10.0 g of dried corn starch and 15.0 g of talc and filled uniformly into 1000 hard gelatin capsules, size 1.

It is possible to use instead of 5-methyl-6-phenylsulphonyl-1,3-benzodioxole-2-carboxylic acid in Examples 39 and 40, a different compound of the general formula I or a pharmaceutically acceptable salt of a compound of the general formula I capable of salt formation, for example one of the compounds described in Examples 3 to 38, or a pharmaceutically acceptable salt of such a compound.

EXAMPLE 41

15.9 g (0.05 mole) of 4-chloro-5-(3-chlorophenylsulfonyl)-1,2-benzenediol, 27.5 g (0.2 mole) of potassium carbonate and 9.67 g (0.075 mole) of dichloroacetic acid are stirred for 6 hours at 100° C. in 125 ml of dimethylformamide. The dimethylformamide is removed by rotary evaporation under a water yet vacuum and the residue is taken up in water. The pH value is adjusted with concentrated hydrochloric acid to 1–2 and the crude acid is extracted with ethyl acetate. The extract is concentrated by evaporation and the residue is dissolved in 150 ml of absolute ethanol. After addition of 0.5 ml of concentrated hydrochloric acid, the batch is heated at reflux for 1 hour. The reaction mixture is then concentrated to a volume of circa 50 ml and allowed to cool. The ethyl 5-chloro-6-(3-chlorophenylsulfonyl)-1,3-benzodioxole-2-carboxylate crystallises from the brown solution in the form of colourless crystals with a melting point of 97°–98° C.

EXAMPLE 42

12.9 g (0.0323 mole) of ethyl 5-chloro-6-(3-methoxyphenylsulfonyl)-1,3-benzodioxole-2-carboxylate are covered with 50 ml of 2-n sodium hydroxide solution and the batch is heated for half an hour in a boiling water bath. After cooling and acidifying the reaction mixture, the 5-chloro-6-(3-methoxyphenylsulfonyl)-1,3 benzodioxole-2-carboxylic acid crystallises. The reaction product is isolated by filtration and recrystallised from ether/toluene, affording crystals with a melding point of 165°–167° C.

(a) The ethyl 5-chloro-6-(e-methoxyphenylsulfonyl)-1,3-benzodioxole-2-carboxylate employed above is obtained in accordance with Example 41 by reacting r-chloro-5-(3-methoxyphenylsulfonyl)-1,2-benzenediol with dichloroacetic acid and potassium carbonate in dimethylformamide and subsequently esterifying the crude acid with ethanol. Melting point 93°–97° C. (crystallization from ethanol).

(b) The 4-chloro-5-(3-methoxyphenylsulfonyl)-1,2-benzenediol employed in Example 2a) is obtained by oxidative coupling of 4-chloro-1,2-benzenediol with 3-methoxybenzenesulfinic acid. Melting point 179°–181° C. (crystallization from ether/toluene).

EXAMPLE 43

22.8 g (0.059 mole) of ethyl 5-chloro-6-(3-fluorophenylsulfonyl)-1,3-benzodioxole-2-carboxylate are covered with 90 ml of 2-n sodium hydroxide solution and the batch is heated for half an hour in a boiling water bath, cooled, acidified with hydrochloric acid and then extracted with ethyl acetate. The extract is concentrated by evaporation, affording 5-chloro-6-(3-fluorophenylsulfonyl)-1,3-benzodioxole-2-carboxylic acid. Melting point 161°–163° C. (crystallisation from ether/toluene).

(a) The ethyl 5-chloro-6-(3-fluorophenylsulfonyl)-1,3-benzodioxole-2-carboxylate employed above is obtained in accordance with Example 1 by reacting 4-chloro-5-(3-fluorophenylsulfonyl)-1,2-benzenediol with dichloroacetic acid and potassium carbonate in dimethylformamide and subsequently esterifying the crude acid with ethanol. Melting point 100°–101° C. (crystallisation from ethanol).

(b) The 4-chloro-5-(3-fluorophenylsulfonyl)-1,2-benzenediol employed in (a) is obtained by oxidiative coupling of 4-chloro-1,2-benzenediol with 3-fluorobenzenesulfinic acid. Melting point 171°–172° C. with decomposition after crystallisation from toluene.

EXAMPLE 44

22.4 g (0.06 Mole) of ethyl 5-(3-fluorophenylsulfonyl)-6-methyl-1,3-benzodioxole-2-carboxylate are covered with 100 ml of 2-n sodium hydroxide solution and the batsch is heated for half an hour in a boiling water bath, cooled and then acidified with hydrochloric acid to a pH value of 1–2. The 5-(3-fluorophenylsulfonyl)-6-methyl-1,3-benzodioxole-2-carboxylic acid is crystallised from toluene. Melting point 177°–180° C.

(a) The ethyl 5-(3-fluorophenylsulfonyl)-methyl-1,3-benzodioxole-2-carboxylate employed above is obtained in accordance with Example 1 by reacting 4-(3-fluorophenylsulfonyl)-5-methyl-1,2-benzenediol with dichloroacetic acid and potassium carbonate in dimethylformamide and subsequently esterifying the crude acid with ethanol. Melting point 83°–85° C. (crystallisation from ethanol).

(b) The 4-(e-fluorophenylsulfonyl)-5-methyl-1,2-benzenediol employed in (a) is obtained in accordance with Example 3a) by oxidative coupling of 4-methyl-1,2-benzenediol with 3-fluorobenzenesulfinic acid. Melting point 168°–174° C. (crystallisation from toluene).

EXAMPLE 45

21.9 g (0.05 mole) of ethyl 5-chloro-6-(3,5-dichlorophenylsulfonyl)-1,3-benzodioxole-2-carboxylate are covered with 75 ml of 2-n sodium hydroxide solution and the batch is heated for 1 hour in a boiling water bath, cooled, acidified with hydrochloric acid and then extracted with ethyl acetate. The extract is concentrated by evaporation, affording 5-chloro-6-(3,5-dichlorophenylsulfonyl)-1,3-benzodioxole-2-carboxylic acid. Melting point 166°–169° C. (crystallisation from ethyl acetate/toluene).

(a) The ethyl 5-chloro-6-(3,5-dichlorophenylsulfonyl)-1,3-benzodioxole-2-carboxylate employed above is obtained in accordance with Example 1 by reacting 4-chloro-5-(3,5-dichloro-phenylsulfonyl)-1,2-benzenediol with dichloroacetic acid and potassium carbonate in dimethylformamide and subsequently esterifying the crude acid in ethanol. Melting point 139°–141° C. (crystallisation from methanol).

(b) The 4-chloro-5-(3,5-dichlorophenylsulfonyl)-1,2-benzenediol employed in (a) is obtained by oxidative coupling of 4-chloro-1,2-benzenediol with 3,5-dichlorobenzenesulfinic acid. Melting point 241°–244° C. (crystallisation from ethyl acetate/toluene).

EXAMPLE 46

10.9 g (0.0264 mole) of ethyl 5-chloro-6-(3,4-methylenedioxyphenylsulfonyl)-1,3-benzodioxole-2-carboxylate are covered with 40 ml of 2-n sodium hydroxide solution and the batch is heated for half an hour in a boiling water bath, cooled, acidified with hydrochloric acid and then extracted with ethyl acetate, affording 5-chloro-6-(3,4-methylenedioxyphenylsulfonyl)-1,3-benzodioxole-2-carboxylic acid. Melting point 182°–184° C. (crystallisation from ethyl acetate/toluene).

(a) The ethyl 5-chloro-6-(3,4-methylenedioxyphenylsulfonyl)-1,3-benzodioxole-2-carboxylate employed above is obtained in accordance with Example 1 by reacting 4-chloro-5-(3,4-methylenedioxyphenylsulfonyl)-1,3-benzenediol with dichloroacetic acid and potassiumcarbonate in dimethylformamide and subsequently esterifying the crude acid with ethanol. Melting point 108°–109° C. (crystallisation from ethanol).

(b) The 4-chloro-5-3-(3,4-methylenedioxyphenylsulfonyl)-1,2-benzenediol employed in (a) is obtained by oxidative coupling of 4-chloro-1,2-benzenediol with 3,4-methylenedioxybenzenesulfinic acid. Melting point 185°–187° C. (crystallisation from toluene).

EXAMPLE 47

8.38 g (0.02 mole) of ethyl 5-(3,5-dichlorophenylsulfonyl)-6-methyl-1,3-benzodioxole-2-carboxylate are covered with 30 ml of 2-n sodium hydroxide solution and the batch is heated for 1 hour in a boiling water bath, cooled and acidified, affording 5-(3,5-dichlorophenylsulfonyl)-6-methyl-1,3-benzodioxole-2-carboxylic acid. Melting point 210°–214° C. (crystallisation from ethyl acetate/toluene).

(a) The ethyl 5-(3,5-dichlorophenylsulfonyl)-6-methyl-1,3-benzodioxole-2-carboxylate employed above is obtained in accordance with Example 1 by reacting 4-(3,5-dichlorobenzenesulfonyl)-5-methyl-1,2-benzenediol with dichloroacetic acid and potassium carbonate in dimethyformamide and subsequently esterifying the crude acid with ethanol. Melting point 135°–137° C. (crystallisation from ethanol).

(b) The 4-(3,5-dichlorophenylsulfonyl)-5-methyl-1,2-benzenediol employed in (a) is obtained by oxidative coupling of 4-methyl-1,2-benzenediol with 3,5-dichlorobenzenesulfinic acid. Melting point from 192° C. in the decomposition after crystallisation from ethyl acetate/toluene.

EXAMPLE 48

35.5 g (0.1 mole) of 5-chloro-6-(3-chlorophenylsulfonyl)-1,3-benzodioxole-2-carboxylic acid are dissolved in 110 ml of acetonitrile. To this solution is added at elevated temperature a solution of 6.7 g (0.055 mole) of triethylamine in 30 ml of acetonitrile. The crystals precipitated from the cooled solution are isolated by filtration and recrystallised twize from methanol, affording the S(—)-1-phenylethylamine salt of (—)-5-chloro-6-(3-chlorophenylsulfonyl)-1,3-benzodioxole-2-carboxylic acid with a melting point of 209°-210° C. After liberation of the acid and recrystallisation from toluene, (—(-5-chloro-6-(3-chlorophenylsulfonyl)-1,3-benzodioxole-2-carboxylic acid is obtained. Melting point 151°-153° C., $[\alpha]_D^{20} - 7°$ (c=1, acetone).

EXAMPLE 49

The process described in Example 48 is repeated using R(+)-1-phenylethylamine as optically active base. (+)-5-chloro-6-(3-chlorophenylsulfonyl)-1,3-benzodioxole-2-carboxylic acid is obtained after salt formation, recrystallisation and liberation of the acid. Melting point 151°-153° C., $[\alpha]_D^{20} + 7°$ (c=1, acetone).

EXAMPLE 50

8.06 g (0.02 mole) of ethyl 5-chloro-6-(3-chlorophenylsulfonyl)-1,3-benzodioxole-2-carboxylate (Example 41) are dissolved at room temperature in 30 ml of dimethylformamide and 1.48 g (0.025 mole) of guanidine base are added. The reaction mixture is allowed to stand for 5 hours at room temperature and is then poured into 200 ml of ice-water. The precipitate is isolated by filtration, dried, digested with ether and then filtered and dried again, affording 5-chloro-6-(3-chlorophenylsulfonyl)-1,3-benzodioxole-2-carboxylic guanidide with a melting point of 125°-130° C.

What is claimed is:
1. A compound of formula I

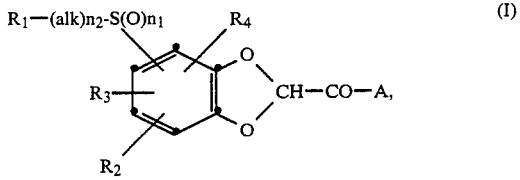

in which $R_1$ represents phenyl, thienyl, furyl or ar-benzothiazolyl, each of which is unsubstituted or substituted a maximum of three times by lower alkyl, lower alkoxy, halogen having an atomic number of up to 35, lower alkanoyl and or by lower alkanoylamino, alk represents alkylene, alkylidene or alkenylene having a maximum of 3 carbon atoms, $R_2$ represents lower alkyl or halogen having an atomic number of up to 35, $R_3$ represents hydrogen, lower alkyl or halogen having an atomic number of up to 35, $R_4$ represents hydrogen and $n_1$ is 1 or 2, $n_2$ is 0 or 1, and A represents the radical —O—$R_5$, wherein $R_5$ represents hydrogen or an aliphatic or araliphatic hydrocarbon radical having, in total, a maximum of 12 carbon atoms, that is unsubstituted or substituted, in a position higher than the 1- or alpha-position, by a halogen having an atomic number of up to 35, hydroxy or by lower alkoxy, or $R_5$ represents a radical

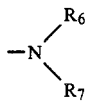

in which $R_6$ and $R_7$ each represents, independently of the other, hydrogen or lower alkyl, or $R_6$ and $R_7$ are bonded to one another and is, together with the adjacent nitrogen atom, an optionally lower alkyl substituted tetra to hexamethylene imino, 4 morpholinyl or 1H-tetrazol-1-yl; and the salts with bases of those compounds in which $R_5$ represents hydrogen.

2. Compounds of the general formula I

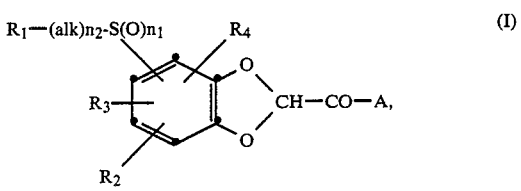

in which $R_1$ represents phenyl or thienyl, each of which is unsubstituted or substituted a maximum of three times by lower alkyl, lower alkoxy, halogen having an atomic number of up to 35, lower alkanoyl and/or by lower alkanoylamino, alk represents methylene, $n_1$ represents 2, $n_2$ represents 0 or 1, $R_2$ represents lower alkyl or halogen, $R_3$ represents hydrogen or lower alkyl, $R_4$ represents hydrogen and A represents $OR_5$ wherein $R_5$ represents hydrogen or lower alkyl, and the pharmaceutically acceptable salts of those compounds in which $R_5$ represents hydrogen with bases.

3. Compounds of the general formula I as claimed in claim 2 in which $R_1$ represents phenyl that is unsubstituted or substituted a maximum of three times by lower alkyl, lower alkoxy and/or by halogen having an atomic number of up to 35, alk represents methylene, $n_1$ represents 2, $n_2$ represents 0 or 1, $R_2$ represents lower alkyl or halogen, $R_3$ represents hydrogen or lower alkyl, $R_4$ represents hydrogen and A represents $OR_5$ wherein $R_5$ represents hydrogen or lower alkyl, and the phenylsulphonyl radical is bonded in the 5- or 6-position, and the pharmaceutically acceptable salts of those compounds in which $R_5$ represents hydrogen with bases.

4. Compounds of the general formula I as claimed in claim 2 in which $R_1$ represents phenyl that is unsubstituted or substituted a maximum of three times by methyl, methoxy and/or chlorine, alk represents methylene, $n_1$ represents 2, $n_2$ represents 0 or 1, $R_2$ represents methyl or chlorine, $R_3$ and $R_4$ represent hydrogen, and A represents $OR_5$ wherein $R_5$ represents hydrogen or lower alkyl, and the phenylsulphonyl radical is bonded in the 5- or 6-position, and the pharmaceutically acceptable salts of those compounds in which $R_5$ represents hydrogen with bases.

5. A compound as claimed in claim 2 being 5-methyl-6-phenylsulphonyl-1,3-benzodioxole-2-carboxylic acid and the pharmaceutically acceptable salts thereof with bases.

6. A compound as claimed in claim 2 being 5-chloro-6-(2-chlorophenylsulphonyl)-1,3-benzodioxole-2-carboxylic acid and the pharmaceutically acceptable salts thereof with bases.

7. A compound as claimed in claim 2 being 5-(2-chlorophenylsulphonyl)-6-methyl-1,3-benzodioxole-2-carboxylic acid and the pharmaceutically acceptable salts thereof with bases.

8. A compound as claimed in claim 2 being 5-chloro-6-(4-chlorophenylsulphonyl)-1,3-benzodioxole-2-carboxylic acid and the pharmaceutically acceptable salts thereof with bases.

9. A compound as claimed in claim 2 being 5-(3-chlorophenylsulphonyl)-6-methyl-1,3-benzodioxole-2-carboxylic acid and the pharmaceutically acceptable salts thereof with bases.

10. A compound as claimed in claim 2 being 5-chloro-6-(3-chlorophenylsulphonyl)-1,3-benzodioxole-2-carboxylic acid and the pharmaceutically acceptable salts thereof with bases.

11. A compound as claimed in claim 2 being (−)-5-chloro-6-(3-chlorophenylsulphonyl)-1,3-benzodioxole-2-carboxylic acid and the pharmaceutically acceptable salts thereof.

12. A compound as claimed in claim 1 being 5-chloro-6-(4-chlorophenylsulphonyl)-1,3-benzodioxole-2-carboxylic acid ethyl ester.

13. A compound as claimed in claim 2 being 5-chloro-6-(3-chlorophenylsulphonyl)-1,3-benzodioxole-2-carboxylic acid ethyl ester.

14. A compound as claimed in claim 2 being 5-chloro-6-(3-methoxyphenylsulphonyl)-1,3-benzodioxole-2-carboxylic acid and the pharmaceutically acceptable salts thereof with bases.

15. A compound as claimed in claim 2 being 5-chloro-6-(3-fluorophenylsulphonyl)-1,3-benzodioxole-2-carboxylic acid and the pharmaceutically acceptable salts thereof with bases.

16. A compound as claimed in claim 2 being 5-(3-fluorophenylsulphonyl)-6-methyl-1,3-benzodioxole-2-carboxylic acid and the pharmaceutically acceptable salts thereof with bases.

17. A compound as claimed in claim 2 being 5-chloro-6-(3,5-dichlorophenylsulphonyl)-1,3-benzodioxole-2-carboxylic acid and the pharmaceutically acceptable salts thereof with bases.

18. A compound as claimed in claim 2 being 5-chloro-6-(3,4-methylenedioxyphenylsulphonyl)-1,3-benzodioxole-2-carboxylic acid and the pharmaceutically acceptable salts thereof with bases.

19. A compound as claimed in claim 2 being 5-(3,5-dichlorophenylsulphonyl)-6-methyl-1,3-benzodioxole-2-carboxylic acid and the pharmaceutically acceptable salts thereof with bases.

20. A pharmaceutical preparation for the treatment of oedema and hypertension comprising an amount, which is an anti-oedema and antihypertensive effective amount, of a compound according to claim 1, or of a pharmaceutically acceptable salt thereof with a base, and at least one pharmaceutically acceptable carrier.

21. A method for treatment of oedema and hypertension in a mammal in need of such treatment comprising oral or parenteral administration of an amount, which is an anti-oedema and antihypertensive effective amount, of a compound according to claim 1, or of a pharmaceutically acceptable salt thereof with a base.

* * * * *